United States Patent
Albert et al.

(10) Patent No.: US 7,575,242 B2
(45) Date of Patent: Aug. 18, 2009

(54) COLLIMATOR CHANGE CART

(75) Inventors: Grant Albert, Elgin, IL (US); Way I. Moy, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 557 days.

(21) Appl. No.: 11/424,769

(22) Filed: Jun. 16, 2006

(65) Prior Publication Data

US 2007/0013273 A1 Jan. 18, 2007

Related U.S. Application Data

(60) Provisional application No. 60/691,324, filed on Jun. 16, 2005.

(51) Int. Cl.
*B62B 3/02* (2006.01)

(52) U.S. Cl. .................... 280/79.3; 280/47.35; 312/333

(58) Field of Classification Search .............. 280/79.3, 280/47.35, 304.1; 312/319, 333
See application file for complete search history.

(56) References Cited

U.S. PATENT DOCUMENTS

| | | | | |
|---|---|---|---|---|
| 3,982,133 A * | 9/1976 | Jupa et al. | ............... | 378/148 |
| 4,865,284 A * | 9/1989 | Gosis et al. | ............... | 248/176.3 |
| 5,519,223 A * | 5/1996 | Hug et al. | ............... | 250/363.1 |
| 5,595,430 A * | 1/1997 | Weyeneth | ............... | 312/319.1 |
| 5,702,167 A * | 12/1997 | Muller | ............... | 312/221 |
| 6,572,122 B2 * | 6/2003 | Johnson et al. | ............... | 280/33.993 |
| 6,590,214 B1 * | 7/2003 | Karmalawy | ............... | 250/363.1 |
| 6,848,759 B2 * | 2/2005 | Doornbos et al. | ............... | 312/319.1 |
| 6,910,557 B2 * | 6/2005 | Doornbos et al. | ............... | 188/290 |
| 6,932,511 B2 * | 8/2005 | Doornbos et al. | ............... | 384/19 |
| 7,108,339 B2 * | 9/2006 | Berger | ............... | 312/333 |
| 2002/0096845 A1 * | 7/2002 | Spann | ............... | 280/79.2 |
| 2004/0065579 A1 * | 4/2004 | Wood | ............... | 206/545 |
| 2004/0104649 A1 * | 6/2004 | Muller et al. | ............... | 312/333 |
| 2004/0262525 A1 * | 12/2004 | Yunker et al. | ............... | 250/363.08 |
| 2006/0017359 A1 * | 1/2006 | Sato et al. | ............... | 312/333 |
| 2006/0186772 A1 * | 8/2006 | Lam et al. | ............... | 312/333 |
| 2007/0013273 A1 * | 1/2007 | Albert et al. | ............... | 312/209 |
| 2007/0103041 A1 * | 5/2007 | Kropf et al. | ............... | 312/333 |
| 2007/0228680 A1 * | 10/2007 | Reppert et al. | ............... | 280/47.35 |
| 2008/0245630 A1 * | 10/2008 | Le | ............... | 188/280 |

\* cited by examiner

*Primary Examiner*—Jeffrey J Restifo

(57) ABSTRACT

An apparatus for operation with a nuclear camera of a nuclear medicine gantry and a patient handling system is provided and includes a cart assembly; and a collimator drawer assembly supported on the cart assembly. The collimator drawer assembly includes a housing; a plurality of collimator drawers slidably supported in housing, wherein each drawer is supported on a rail provided on opposed sides of said drawer; a damper operatively connected to each drawer; and a drawer locking mechanism movable from a first position in which all the drawers are prevented from sliding out of the housing and a second position in which all of the drawers are free to slide out of the housing. The collimator drawer assembly further includes an anti-tip over feature.

17 Claims, 22 Drawing Sheets

COLLIMATOR CHANGE CART

CROSS-REFERENCE TO RELATED APPLICATION

The present application claims the benefit of and priority to U.S. Provisional Application Ser. No. 60/691,324, filed on Jun. 16, 2005, the entire content of which is incorporated herein by reference.

BACKGROUND

1. Technical Field

The present disclosure relates to the field of gamma cameras used in the area of nuclear medicine and, more particularly to collimator storage devices, exchange devices and carts.

2. Background of Related Art

Nuclear or scintillation cameras (also called gamma cameras) are responsive to radiation emitted from a radiopharmaceutical injected into a patient during an imaging study. A radiopharmaceutical is typically selected that will target a particular organ or tissue of interest. In computed tomography studies, a detector head (or pair of heads) revolves around the patient and collects the emissions at various angles in order to generate an image of the targeted organ or tissue. In total body studies, the detectors may translate at a fixed or variable altitude along the patient.

In Emission Computed Tomography (ECT) studies, the image data collected at each angle is merged together into a database that is representative of a three dimensional image of the targeted organ or tissue by a mathematical procedure called reconstruction tomography. A computer process and system perform the image data collection and tomography, and the resultant images may be displayed in a variety of fashions on a computer controlled display screen. Gamma camera detectors are also used in many types of studies that do not employ tomography for image generation, such as total body studies.

Each detector head of a gamma camera utilizes a collimator placed in front of the detector mechanism to respond to the incident emissions. The collimator is a device for collimating the incident radiation emissions and for filtering out certain types of unwanted radiation emissions. A collimator is typically manufactured from lead material and is composed of an array of parallel tubes and as such resembles a lead "honeycomb." Each individual collimator may weigh from 100 to 250 pounds or more and is mounted on the receiving end of the gamma camera detector to cover the imaging surface. Each collimator must be securely fastened to the detector head during gamma camera studies to prevent collimator separation from the imaging surface as the detector heads revolve or rotate.

Different collimators have particular characteristics suited to the patient study and the energy of the radiation emissions from the ingested radiopharmaceutical. For instance, some collimators are better suited for gamma studies of a given energy range, a given emission exposure duration, or a given radiopharmaceutical.

Typically, a nuclear camera includes a family of collimators. Relatively thicker collimators with small bores provide higher resolution. Relatively thinner collimators and collimators with larger bores provide higher count rates. Collimators whose bores are angled are used for magnification and reduction imaging. Specialized collimators that focus on two displaced regions of the subject are also used.

In many instances, the collimators need to be changed depending on the particular procedure being performed and to maintenance purposes. To change the collimators, the operator moves the detector heads to the appropriate collimator changing position. The operator then rolls in a collimator holding cart, which supports the currently installed collimators as they are disconnected. The cart is then used to transport the collimators to a storage location where it is further used to pick-up the proper set of collimators. The appropriate set of collimators on the cart are wheeled up to the detector heads and manually mechanically coupled. This operation typically requires 10-15 minutes of operator time.

Accordingly, a continuing need exists for carts or carriages for facilitating the removal, replacement and/or exchange of collimators from a nuclear camera and the like.

SUMMARY

The present disclosure relates to collimator storage devices, exchange devices and carts.

According to an aspect of the present disclosure, a collimator change cart for operation with a nuclear camera of a nuclear medicine gantry and a patient handling system is provided. The collimator change cart includes a cart assembly; and a collimator drawer assembly supported on the cart assembly. The collimator drawer assembly includes a housing; a plurality of collimator drawers slidably supported in housing, wherein each drawer is supported on a rail provided on opposed sides of said drawer; and a damper operatively connected to each drawer. The damper functions to slow extension and retraction of drawers into and out of the housing.

The collimator drawer assembly may further include a pusher operatively associated with each drawer. The pusher may cause the drawer to extend uniformly from the housing. Each damper may be a hydraulic fluid damper. Each velocity damper may include a first end connected to a respective drawer and a second end connected to the housing.

The collimator drawer assembly may include a drawer locking mechanism movable from a first position in which all the drawers are prevented from sliding out of the housing and a second position in which all of the drawers are free to slide out of the housing. The drawer locking mechanism may include an actuator bar supporting a plurality of tabs thereon. The actuator bar may be movable between the drawer locking mechanism first position and second position. The tabs may be movable between the drawer locking mechanism first position and second position as the actuator bar is moved between the drawer locking mechanism first position and second position. Each tab may engage a respective drawer when the drawer locking mechanism is in the first position.

The drawer locking mechanism may include a lock plunger extending from a bottom of the housing. The lock plunger may be actuatable to move the drawer locking mechanism between the first and second positions. The lock plunger may engage a lock receptacle on the patient handling system and may inhibit tipping of the collimator change cart when the collimator change cart is docked.

The collimator change cart may further include an anti-tip over feature supported on the patient handling system and configured to engage the cart assembly when the collimator change cart is docked. The anti-tip over feature may include a channeled rail supported on the patient handling system and configured and dimensioned to selectively receive at least a portion of the cart assembly therein. The anti-tip over feature may further include a plunger extending from a bottom surface of the housing of the collimator change cart. The plunger may operatively engage a pallet of the patient handling system when the pallet is in a raised position.

The collimator change cart may further include a drawer locking mechanism movable from a first position in which all the drawers are prevented from sliding out of the housing and a second position in which all of the drawers are free to slide out of the housing. The drawer locking mechanism may include an actuator bar supporting a plurality of tabs thereon, wherein the actuator bar may be movable between the drawer locking mechanism first position and second position. The plunger may be connected to the drawer locking mechanism such that the plunger may be actuatable to move the drawer locking mechanism between the first and second positions.

The cart assembly may include a pair of spaced apart lower rails supports on casters. The cart assembly may further include an upper platform cantilevered with respect to an upright extending from the lower rails.

According to another aspect of the present disclosure, a collimator change cart for operation with a nuclear camera of a nuclear medicine gantry and a patient handling system is provided. The collimator change cart includes a cart assembly; and a collimator drawer assembly supported on the cart assembly. The collimator drawer assembly includes a housing; a plurality of collimator drawers slidably supported in housing, wherein each drawer is supported on a rail provided on opposed sides of said drawer; a damper operatively connected to each drawer, wherein the damper slows extension and retraction of drawers into and out of the housing; and a drawer locking mechanism movable from a first position in which all the drawers are prevented from sliding out of the housing and a second position in which all of the drawers are free to slide out of the housing. The collimator change cart further includes an anti-tip over feature supported on the patient handling system and configured to engage the cart assembly when the collimator change cart is in an operative position relative to the nuclear medicine gantry and the patient handling system.

BRIEF DESCRIPTION OF THE DRAWINGS

The invention may take physical form in certain parts and arrangements of parts, a preferred embodiment of which will be described in detail herein and illustrated in the accompanying drawings which form a part hereof and wherein.

DETAILED DESCRIPTION OF EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
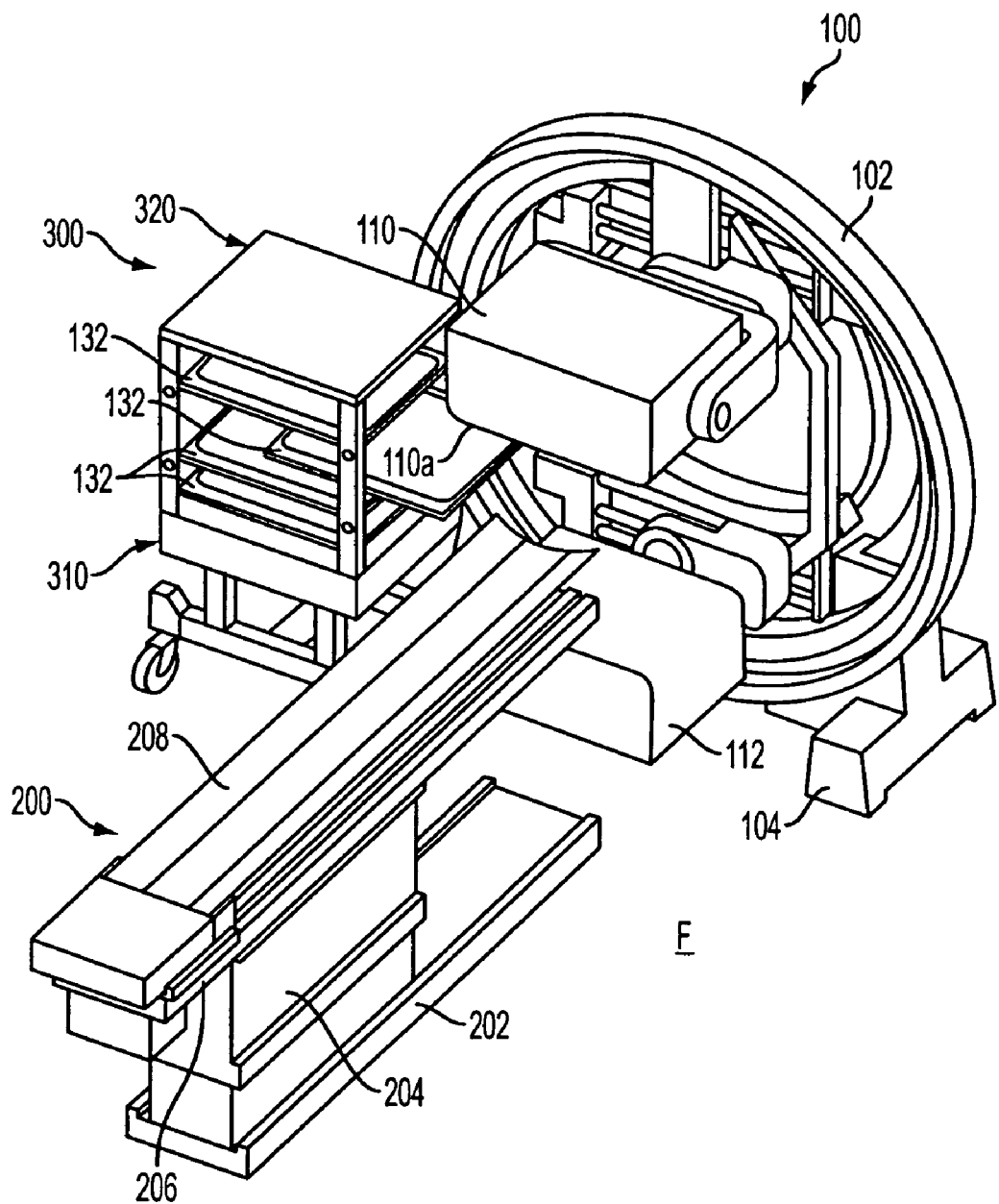
FIG. 1 is a schematic, perspective view of a collimator change cart of the present disclosure as used with a nuclear medicine gantry and a patient handling system.
Figure 2:
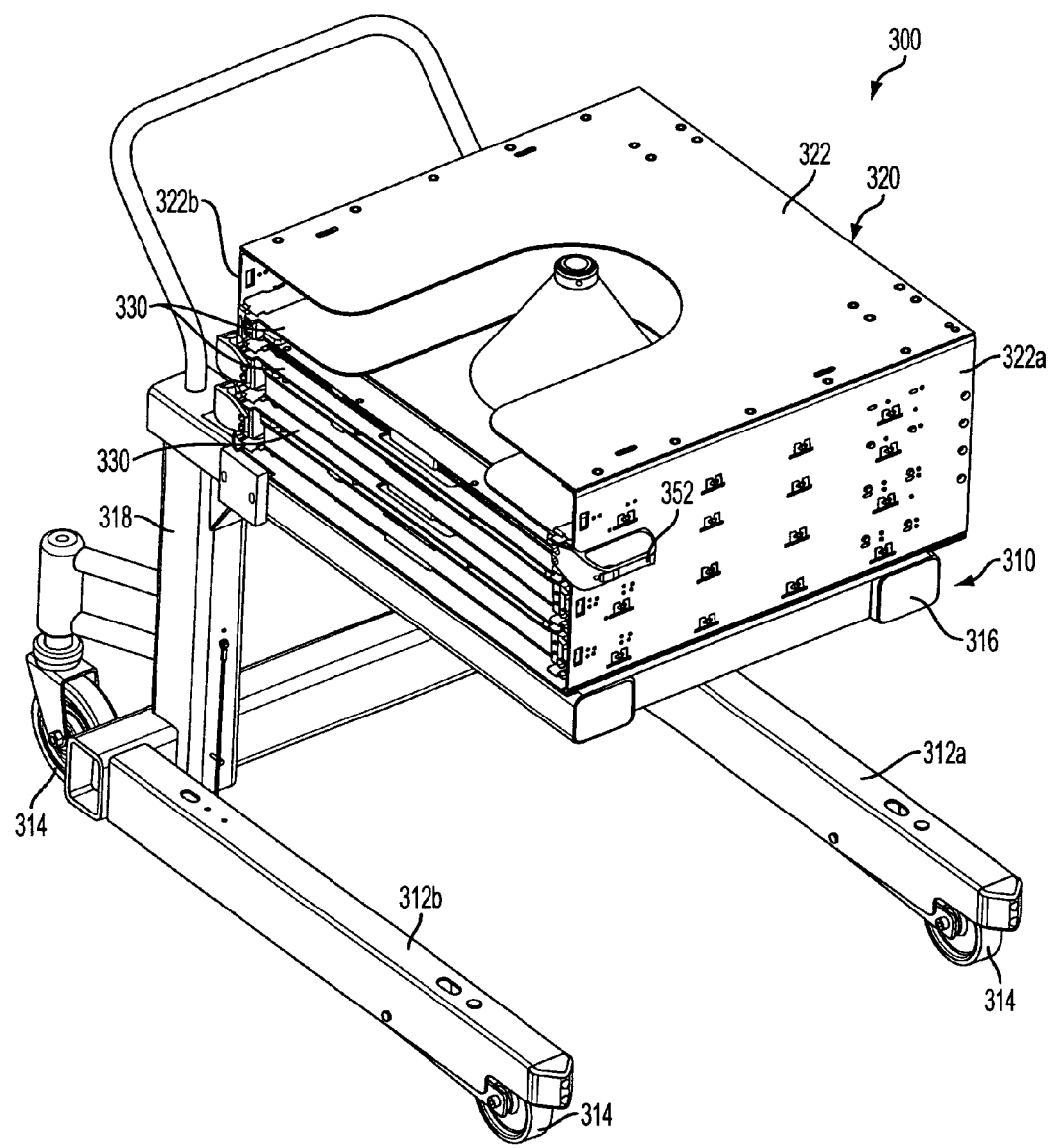
FIG. 2 is an enlarged perspective view of the collimator change cart of FIG. 1, illustrating the collimator change cart in a first condition.
Figure 3:
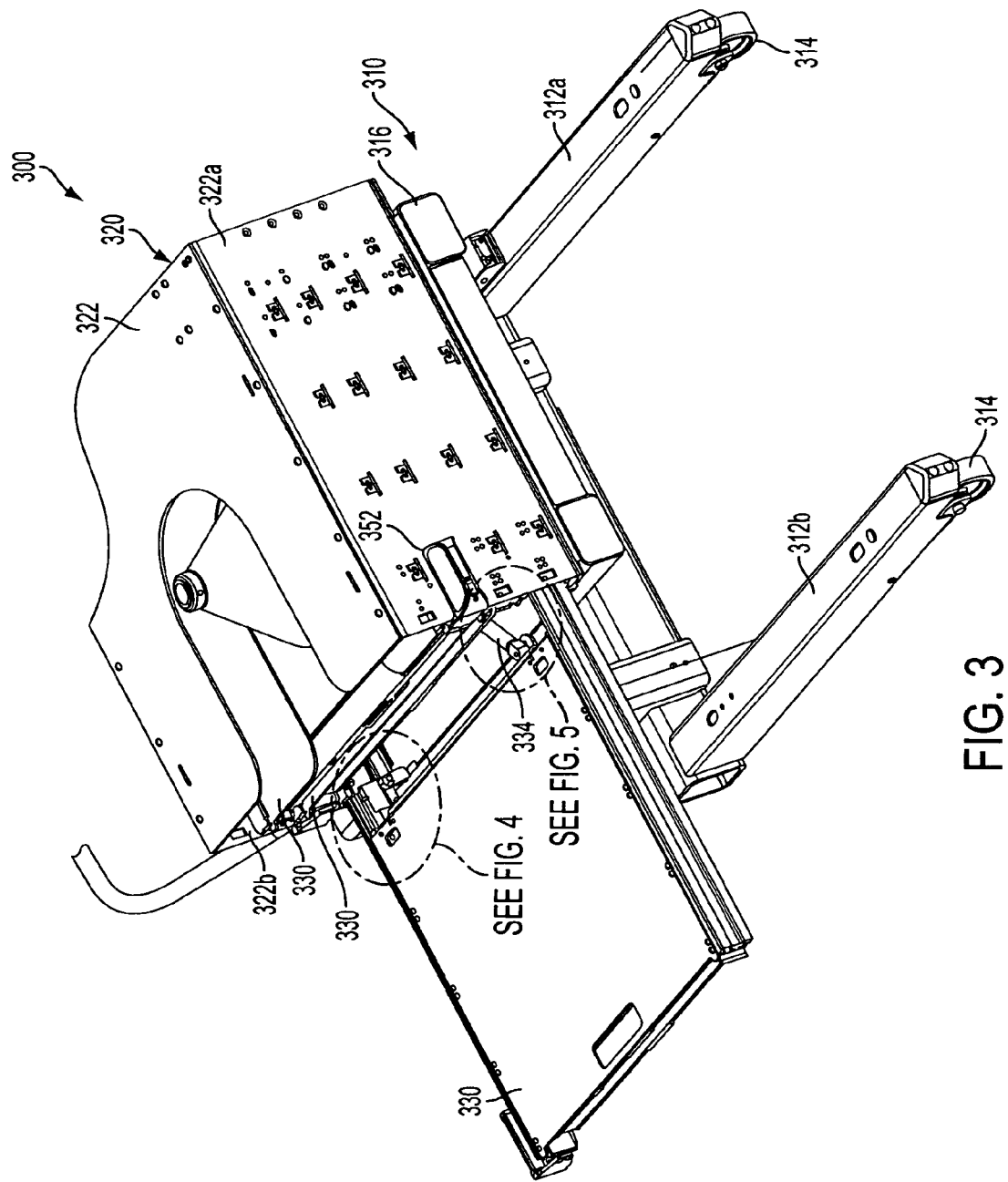
FIG. 3 is an enlarged view of the collimator change cart of FIG. 2, illustrating the collimator change cart in a second condition.
Figure 5:
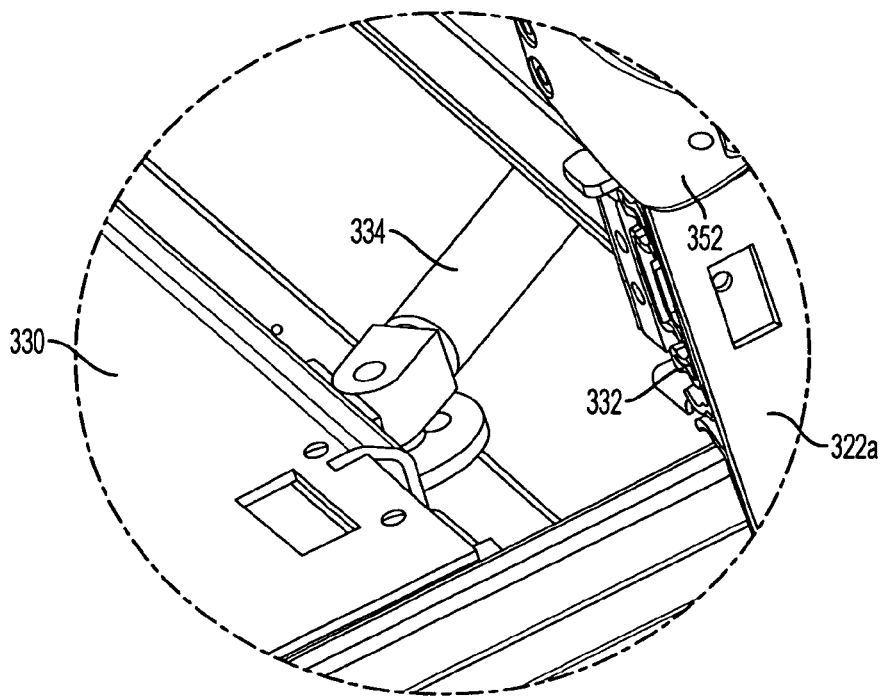
FIG. 5 is an enlarged, perspective view of the indicated area of detail of FIG. 3, illustrating an end of a velocity damper of the collimator change cart of FIGS. 1-3.

Referring now to the drawings, and first to FIG. 1, a nuclear medicine gantry 100 and patient handling system 200 are shown. Nuclear medicine gantry 100 includes a ring 102 operatively connected to and supported on a stand 104. Nuclear medicine gantry 100 further includes a first nuclear camera 110 and a second nuclear camera 112, each, operatively associated with and/or mounted to ring 102.

Patient handling system 200 includes a lower frame 202 supported on floor "F", a lift mechanism 204 operatively supported on lower frame 202, an upper frame 206 operatively supported on lift mechanism 204 and a pallet 208 translatably supported on upper frame 206. Patient handling system 200 may be oriented such that pallet 208 is translatable in directions parallel to a central axis of ring 102. Lift mechanism 204 (e.g., parallelogram style, scissors style, etc.) provides the up and down motion of upper frame 206 and pallet 208 for patient loading and positioning.

As seen in FIG. 1, nuclear medicine gantry 100 and patient handling system 200 can accommodate use of a collimator change cart 300. With reference to FIGS. 2-6, Collimator change cart 300 includes a cart assembly 310 supporting a collimator drawer assembly 320 housing and/or storing a plurality of collimators 132 therein. Cart assembly 310 includes a pair of spaced apart lower rails 312a, 312b supported on casters 314 or the like and an upper platform 316 connected to lower rails 312a, 312b by a pair of uprights 318. Upper platform 316 is cantilevered with respect to uprights 318 and is configured and adapted to support collimator drawer assembly 320 thereon.

As seen in FIGS. 2-6, collimator drawer assembly 320 includes a housing 322 having at least a pair of spaced apart side walls 322a, 322b, and optionally a top wall 322c. In one embodiment, the pair of spaced apart side walls 322a, 322b are oriented orthogonal to lower rails 312a, 312b of cart 310. Collimator drawer assembly 320 is configured and adapted to support at least one drawer 330 thereon, between side walls 322a, 322b. Each drawer 330 is slidably mounted within housing 322 and has a first position fully retracted within housing 322 and a second position extending from housing 322 in a cantilevered manner. Collimator drawer assembly 320 may be configured to support any number of drawers 330 therein.

Each drawer 330 may be operatively connected to rails 332 supported on side walls 322a, 322b. Each rail 332 may consist of a linear rail system having a first component thereof supported on a side wall and a second component thereof supported on the drawer, wherein the first and second components of the linear rail system are slidably supported relative to one another. Each drawer 330 is configured to support a collimator 132 (see FIG. 1) thereon. It is contemplated that each drawer 330 may support a different collimator thereon as compared to the other drawers.

As seen in FIGS. 3, 5, 6, 8, 9, 14, 15, 22 and 23, collimator drawer assembly 320 includes a velocity damper 334 connected to each drawer 330. Velocity damper 334 may be a hydraulic fluid damper including a first end connected to a drawer 330 and a second end connected to housing 322, wherein the first end and the second end of each damper 334 is fluidly connected to one another. In this manner, as drawer 330 is pulled from housing 322, damper 334 functions to maintain exert a consistent damping force on drawer 330 to prevent drawer 330 from opening and/or closing too quickly.

As seen in FIGS. 3, 4-4C and 23, collimator drawer assembly 320 further includes a drawer pusher assembly 336 operatively associated with each drawer 330 and with each respective rail 332 thereof (i.e., the right-side rail and the left side rail). Drawer pusher assembly 336 functions to move drawer 330 out from housing 322 in a uniform manner with respect to the pair of juxtaposed rails 332. In other words, since right-side and left-side rails 332 are independent of one another, drawer pusher assembly 336 functions to move right-side and left-side rails 332 in unison with one another to ensure that drawer 330 is withdrawn uniformly from housing 322.

Figure 4:
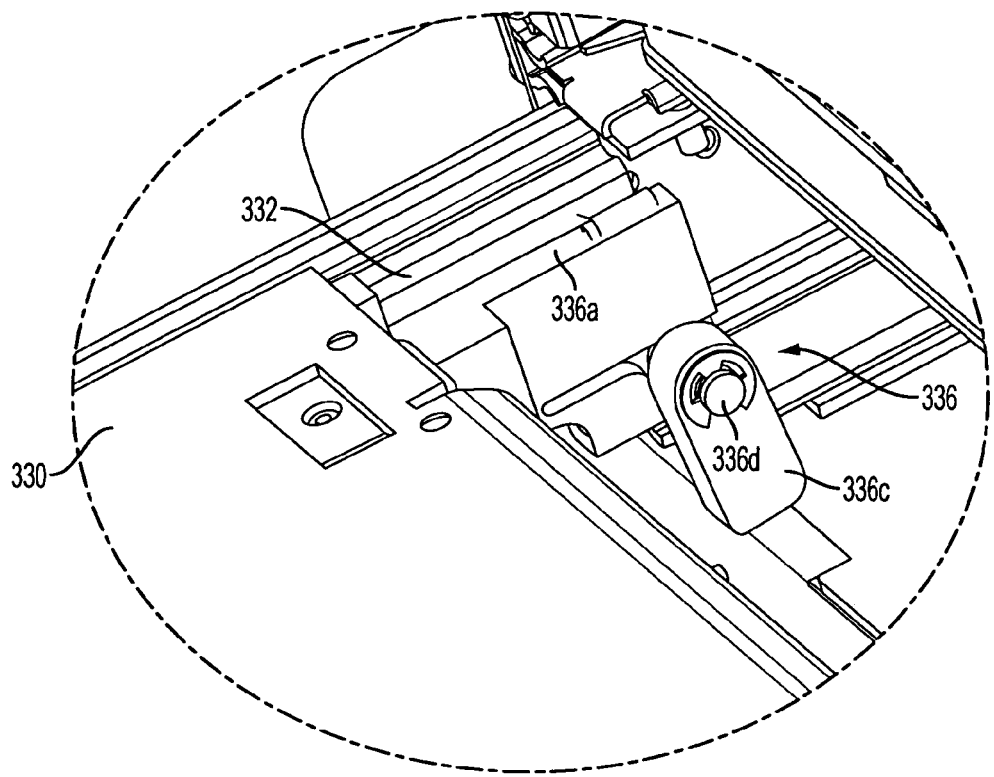
FIG. 4 is a further enlarged view of the indicated area of detail of FIG. 3, illustrating a drawer pusher assembly of the collimator change cart of FIGS. 1-3.
Figure 4A:
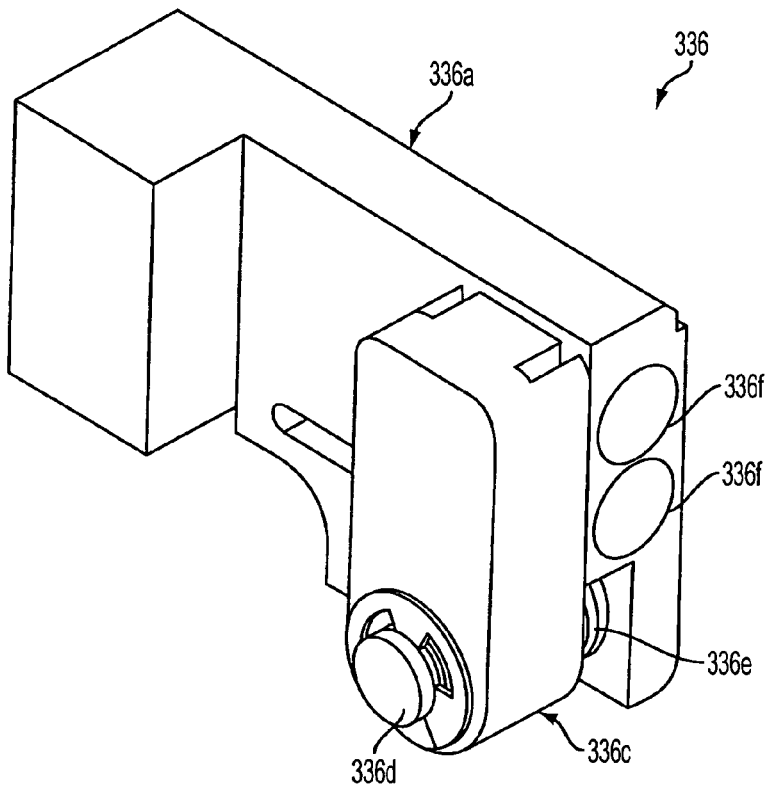
FIG. 4A is a perspective view of the drawer pusher assembly of FIG. 4.
Figure 4B:
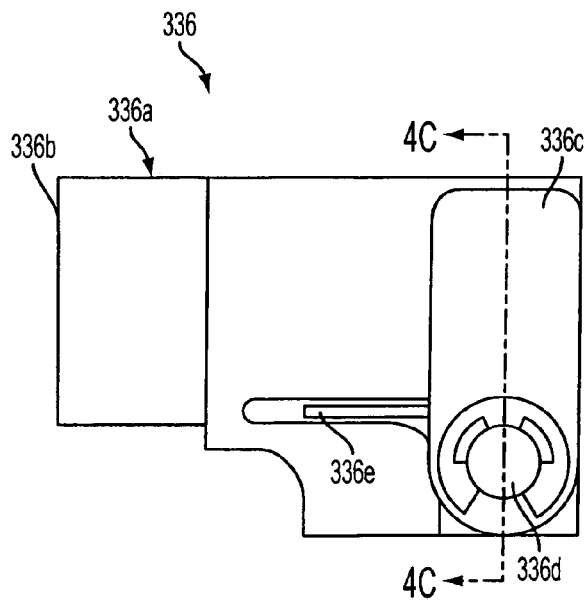
FIG. 4B is an elevational view of the drawer pusher assembly of FIG. 4A.
Figure 4C:
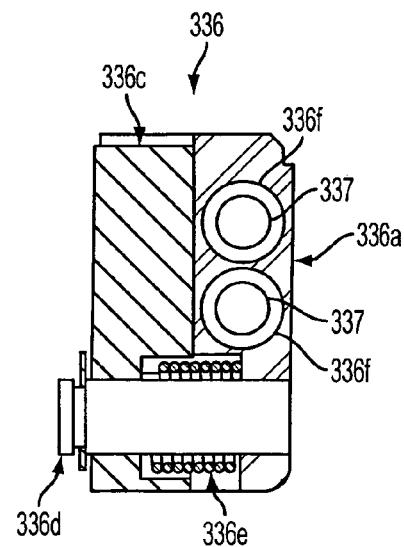
FIG. 4C is a cross-sectional view of the drawer pusher assembly of FIG. 4B, as taken through 4C-4C thereof.

As seen in FIGS. 4A-4C, drawer pusher assembly 336 includes block pusher 336a connected to a portion of rail 332 connected to drawer 330. Drawer pusher assembly 336 further includes a pusher arm 336c pivotally connected to block pusher 336a via a pivot shaft 336d. Drawer pusher assembly 336 includes a biasing member 336e supported on pivot shaft 336d and operative engaged with block pusher 336a and pusher arm 336c.

In operation, when drawer 330 is fully retained within housing 322, pusher arm 336c is in an upright condition, as seen in FIGS. 4A-4C and biasing member 336e is in a biased condition. As drawer 330 is withdrawn from housing 322, pusher arm 336c is pivoted about pivot shaft 336d by the spring force and the unwinding of biasing member 336e. As pusher arm 336c is pivoted about pivot shaft 336d, block pusher 336a moves the portion of rail 332 attached to drawer 330 to facilitate withdrawal of drawer 330 from housing 322 and ensure uniform simultaneous extension of the right-side and left-side rails.

In particular, in one embodiment, a pair of through-bores 336f are formed through block pusher 336a for slidably receiving a pair of shafts or guides 337 therethrough. Accordingly, as pusher arm 336c is pivoted about pivot shaft 336d, block pusher 336a is moved axially along the pair of shafts or guides.

Figure 6:
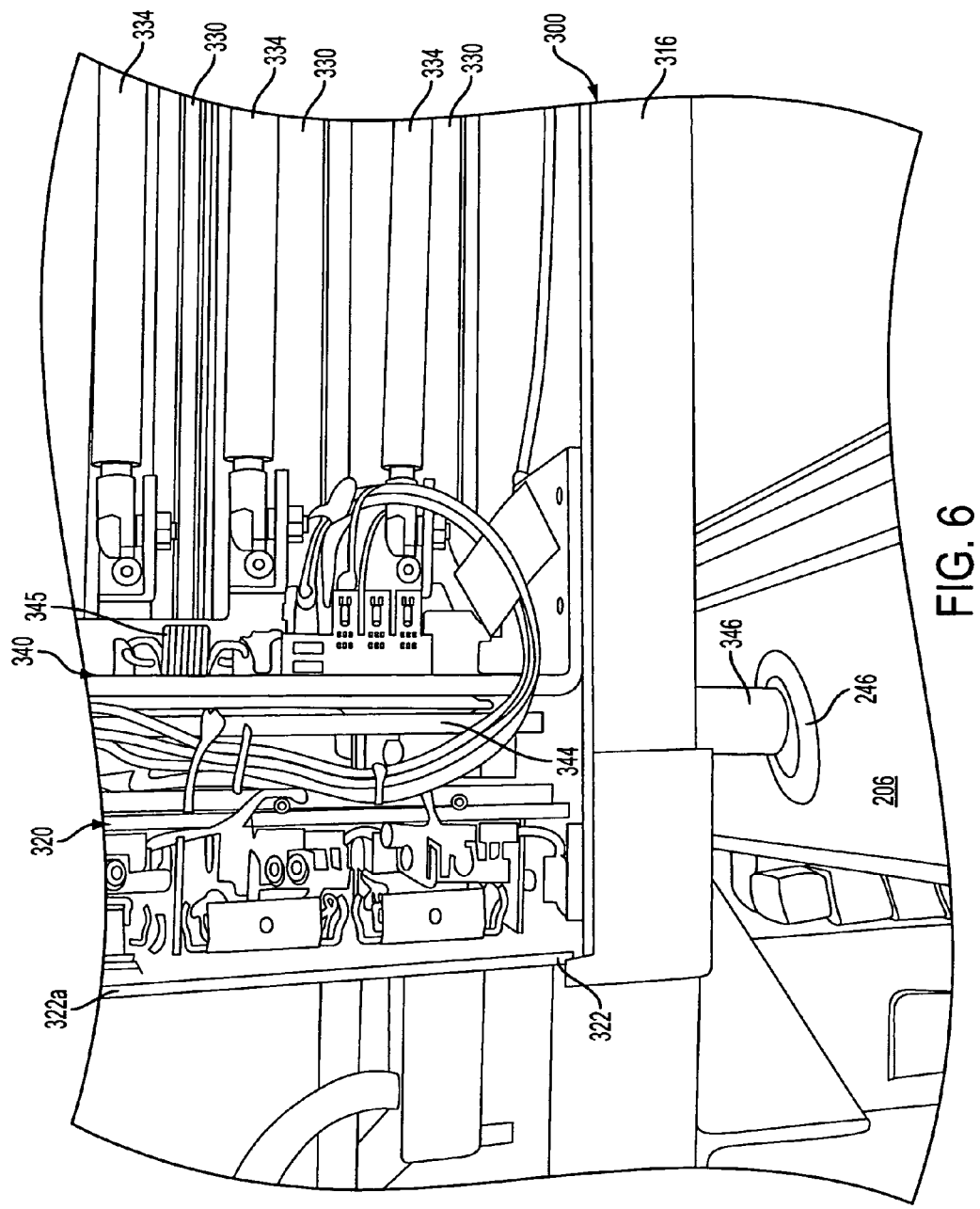
FIG. 6 is a rear view of a collimator drawer assembly of the collimator change cart of FIGS. 1-3.
Figure 7:
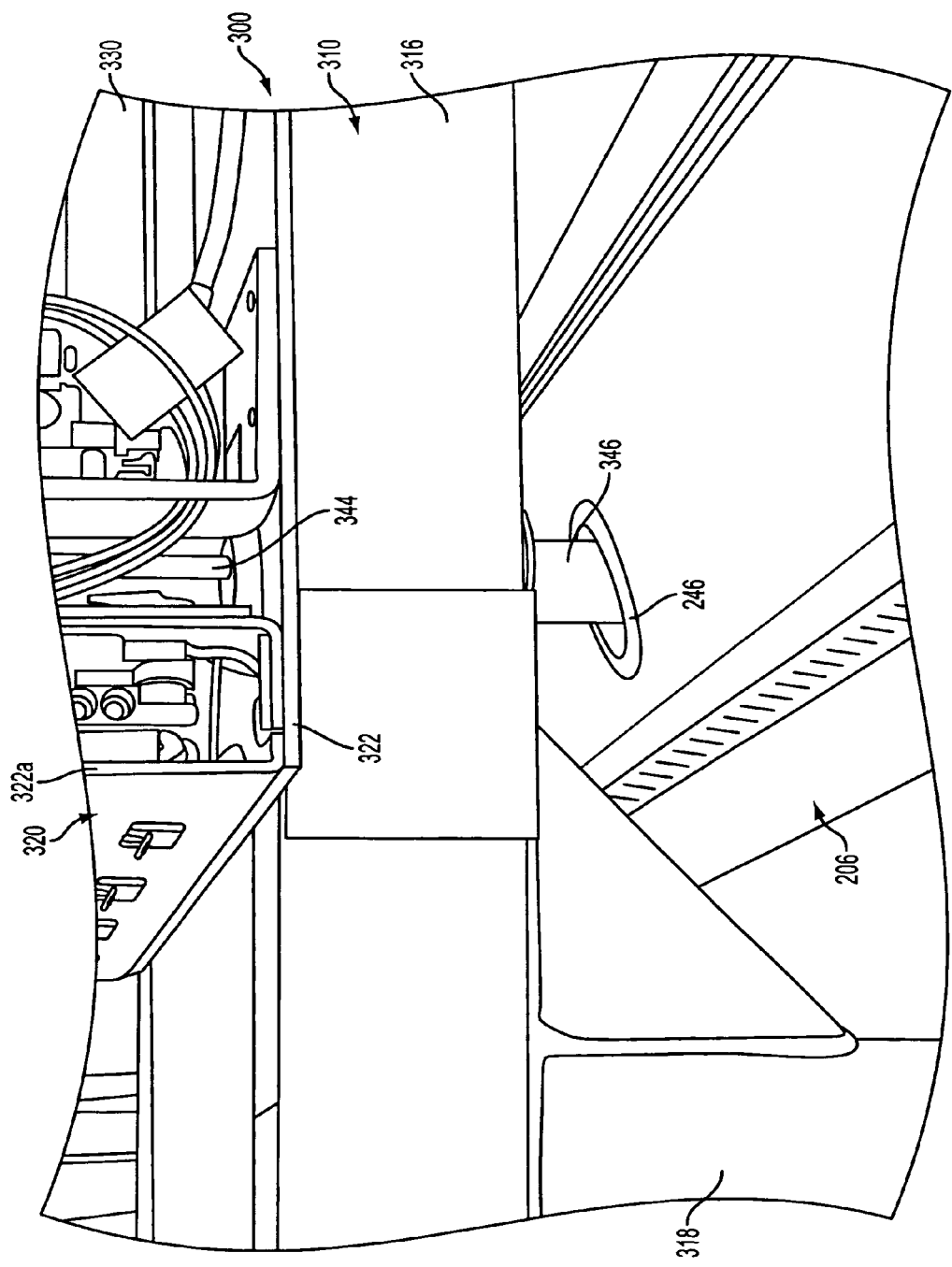
FIG. 7 is a partial perspective view of the nuclear medicine gantry operatively engaged with a lock plunger of the collimator change cart of FIGS. 1-3.
Figure 8:
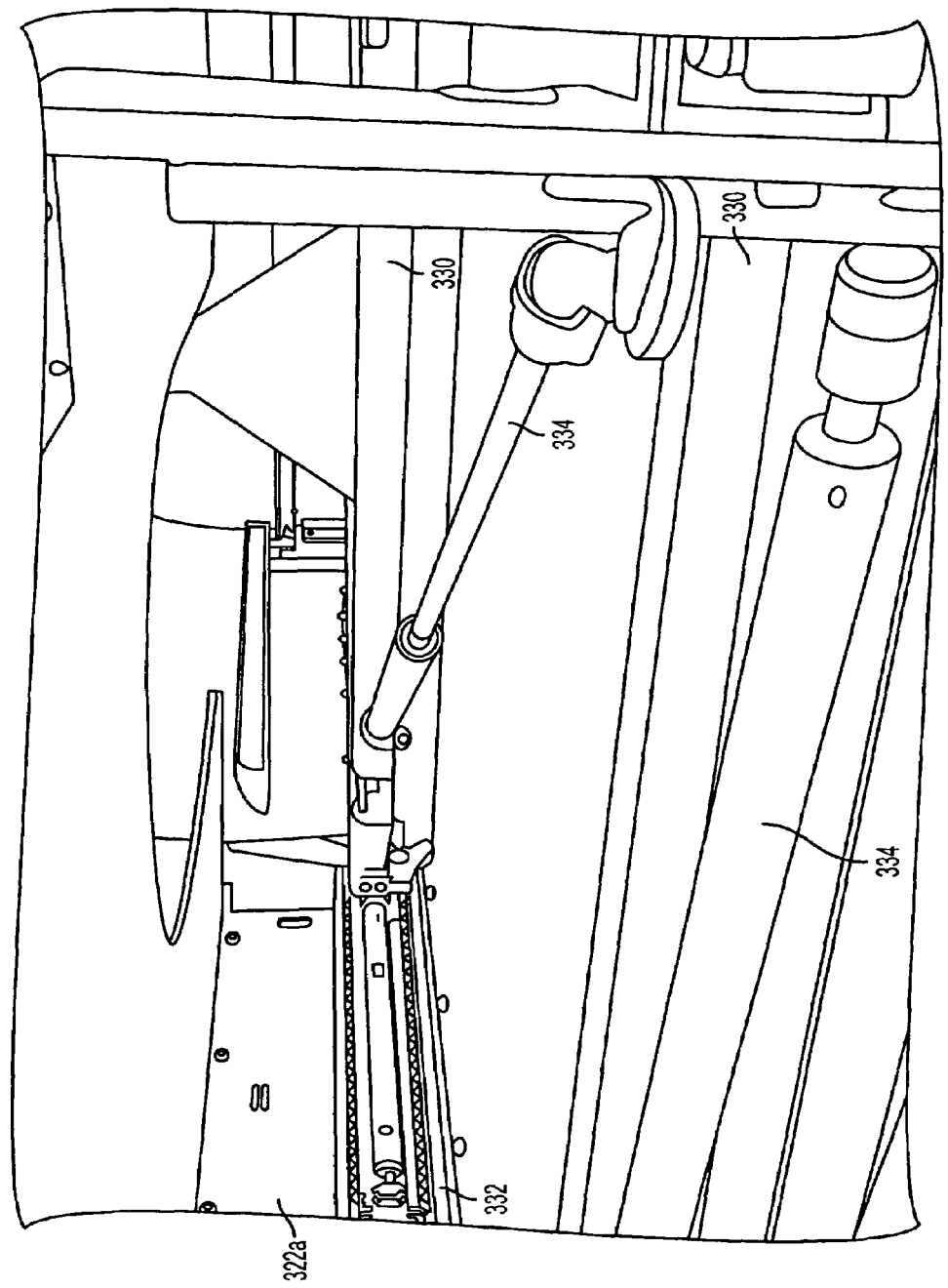
FIG. 8 is a partial perspective view of collimator drawer assembly of the collimator change cart of FIGS. 1-3, illustrating a drawer thereof and a corresponding velocity damper thereof in an extended condition.
Figure 9:
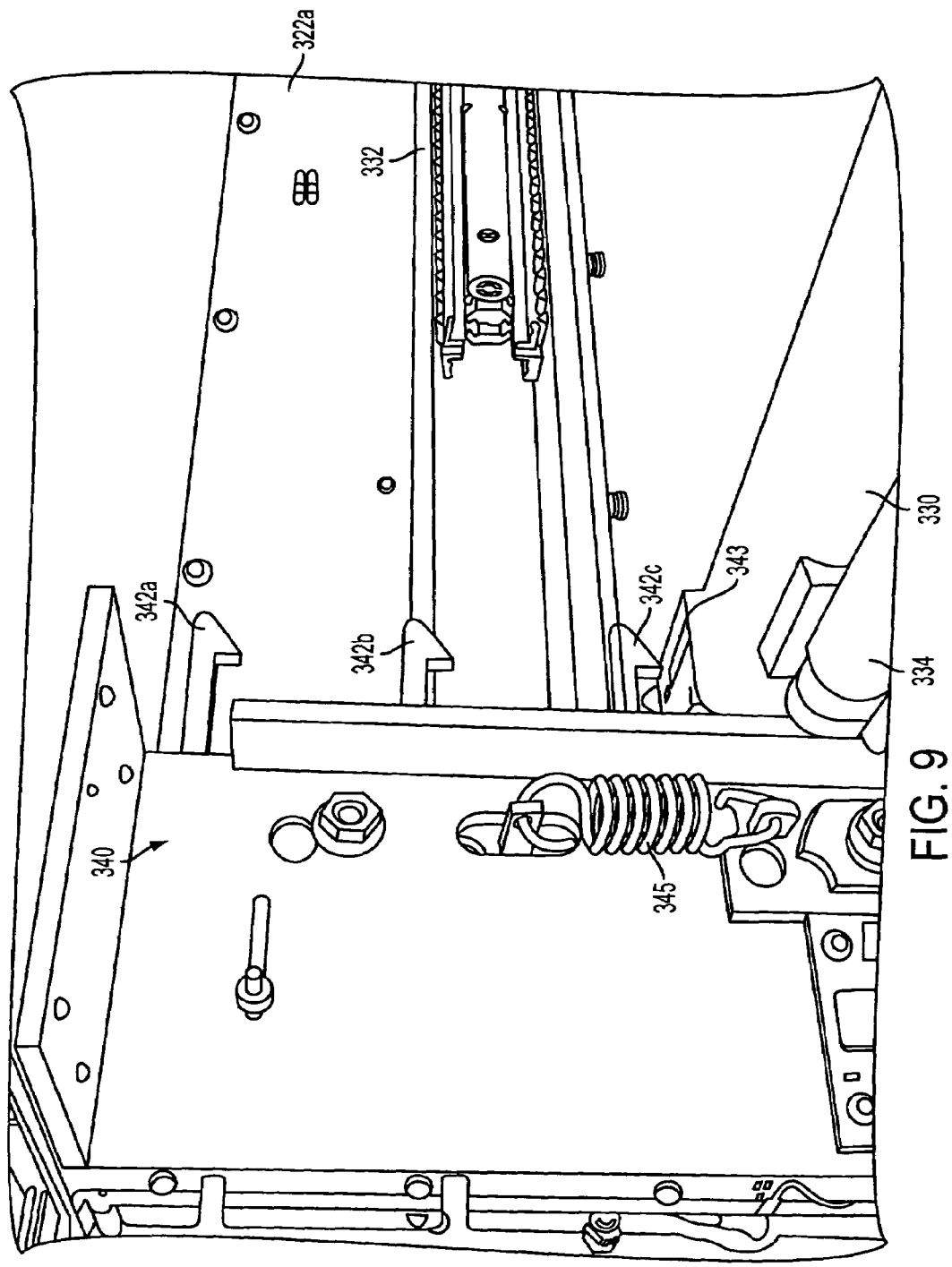
FIG. 9 is a partial perspective view of a locking mechanism of the collimator chance cart of FIGS. 1-3, shown in an unlocked position.

As seen in FIGS. 6, 7 and 9, collimator drawer assembly 320 includes a drawer locking mechanism 340. Drawer locking mechanism 340 includes a respective locking tab 342a-342c for each drawer 330. Drawer locking mechanism 340 is movable between a first position in which locking tabs 342a-342c are engaged with a respective aperture 343 formed in drawer 330 and a second position in which locking tabs 342a-342c are disengaged from a respective drawer 330. Locking tabs 342a-342c are supported on an actuator bar 344 and are capable of moving simultaneously. Drawer locking mechanism 340 further includes a lock plunger 346 operatively connected to actuator bar 344 and extending beneath housing 322, and preferably, platform 316. Drawer locking mechanism 340 may be biased to the first position by a spring member 345.

In operation, as will be discussed in greater detail below, lock plunger 346 includes an extended position wherein drawer locking mechanism 340 is in the first position and locking tabs 342a-342c are in operative locking engagement in respective apertures 343 of drawers 330, and a retracted position, as seen in FIG. 9, wherein drawer locking mechanism 340 is in the second position and locking tabs 342a-342c are out of operative locking engagement with respective apertures 343 of drawers 330.

Figure 10:
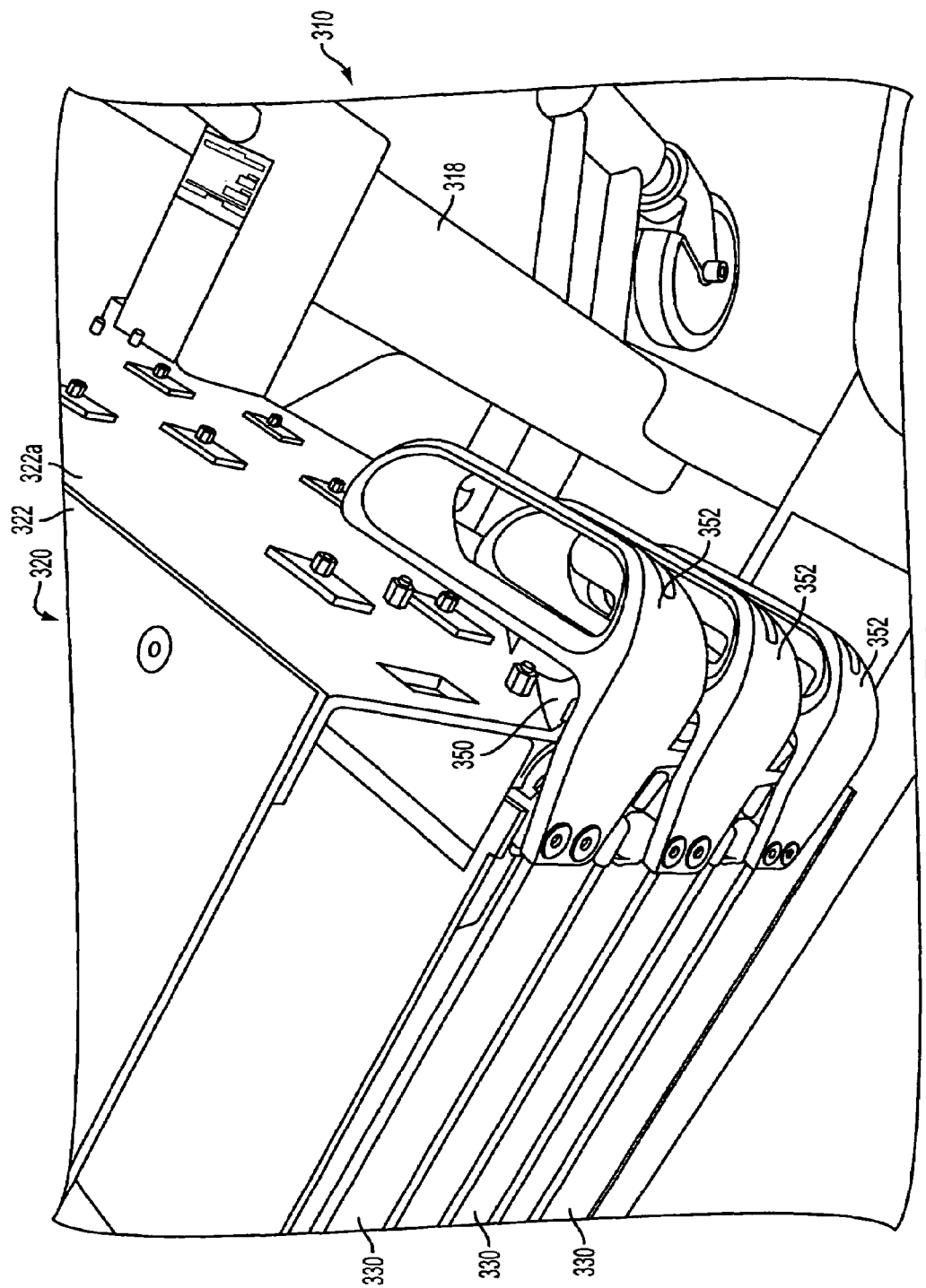
FIG. 10 is a partial perspective view of a drawer locking assembly of the collimator change cart of FIGS. 1-3.

As seen in FIG. 10, collimator drawer assembly 320 further includes a drawer lock 350 operatively associated with each drawer 330. Each drawer lock 350 includes a handle 352 supported on each drawer 330a-330d and a resilient tab 354 extending from each handle 352 and snap-fit engaging a side wall 322, 322b of housing 322 when drawers 330 are in a fully closed position. In operation, in order to release a drawer 330, resilient tab 354 is deflected away from a corresponding tab (not shown) on housing 322 and handle 352 is used to pull said drawer 330 from housing 322.

As seen in FIGS. 6, 7, 11 and 14-17, collimator change cart 300 includes an anti-tip over element 360 which is secured to the floor, nuclear medicine gantry 100 or patient handling system 200. In the present embodiment, anti-tip over element 360 includes a channeled rail 362, or the functional equivalent thereof operatively connected to patient handling system 200, at a location in close proximity to the floor. Channeled rail 362 is configured and dimensioned such that at least one of lower rails 312a, 312b of cart assembly 310 is introducible therein. In operation, when a lower rail 312a, 312b of cart assembly 310 is operatively inserted into channeled rail 362, channeled rail 362 functions to anchor lower rail 312a or 312b of cart assembly 310 to the ground and thus functions to inhibit and/or prevent cart assembly 310 from tipping over during use and/or operation of collimator change cart 300.

Figure 12:
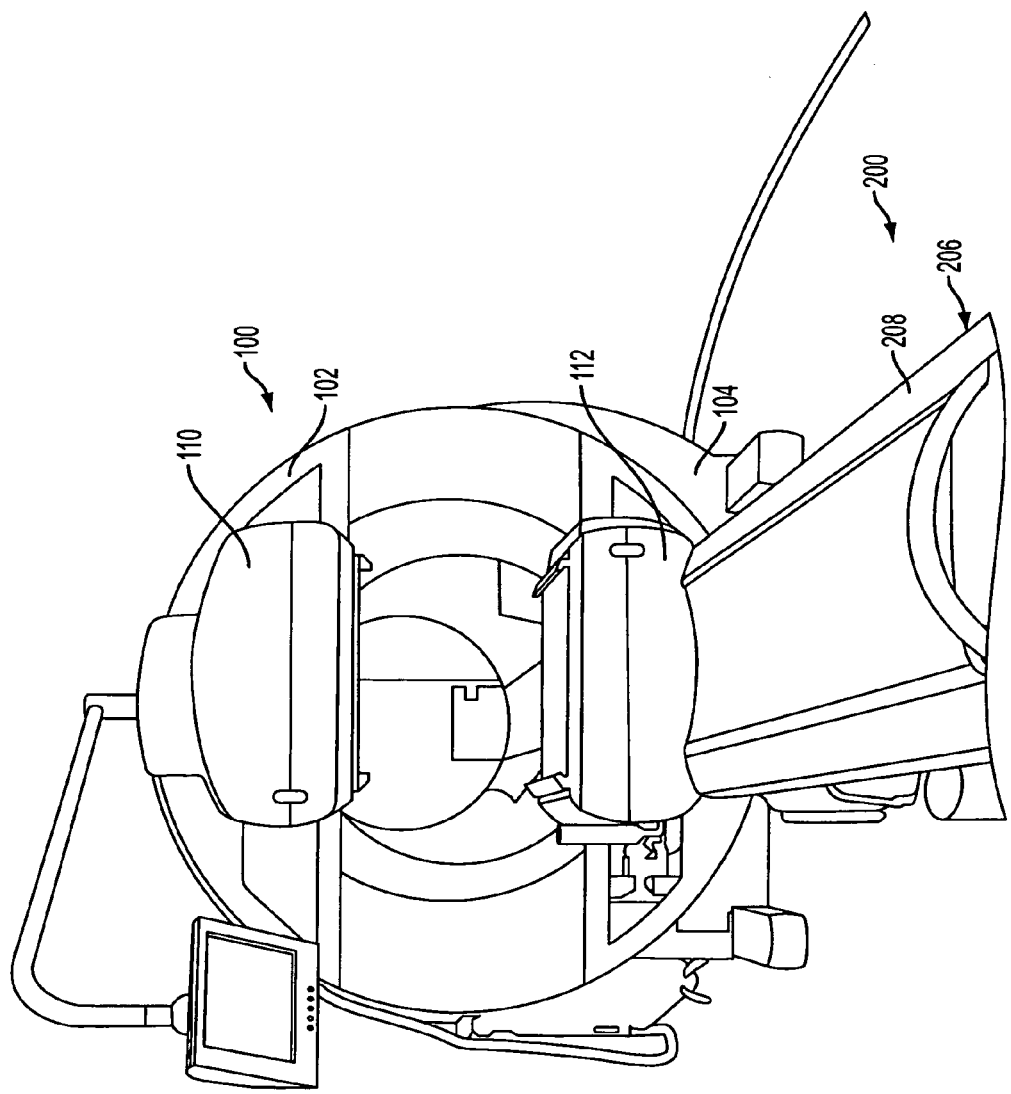
FIG. 12 is a partial perspective view of the nuclear medicine gantry and patient handling system of FIG. 1, shown in a "home" position.
Figure 13:
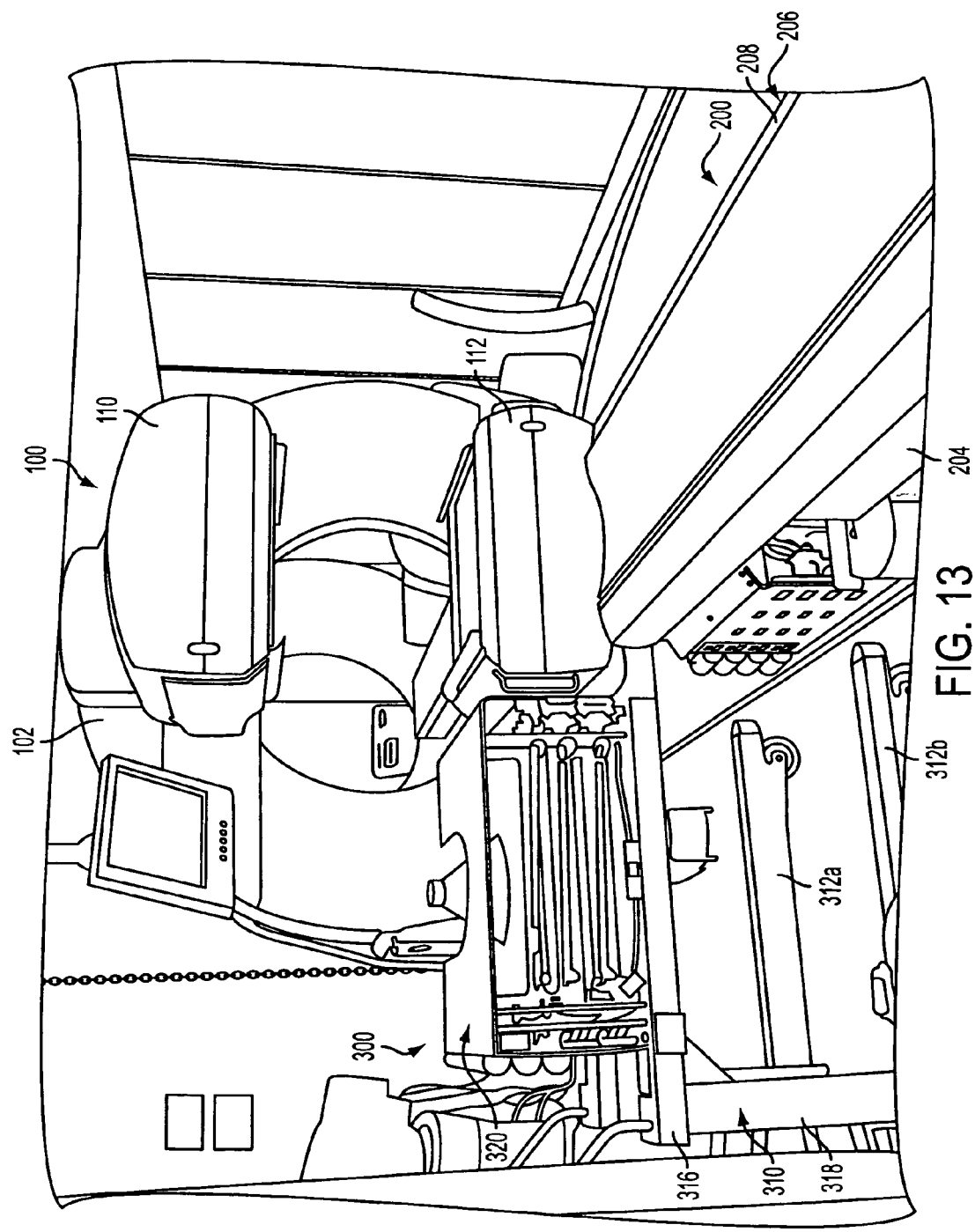
FIG. 13 is a partial perspective view of the nuclear medicine gantry and patient handling system of FIGS. 1 and 12, illustrating a relative positioning of the collimator change cart of FIGS. 1-3 thereto prior to docking therewith.
Figure 14:
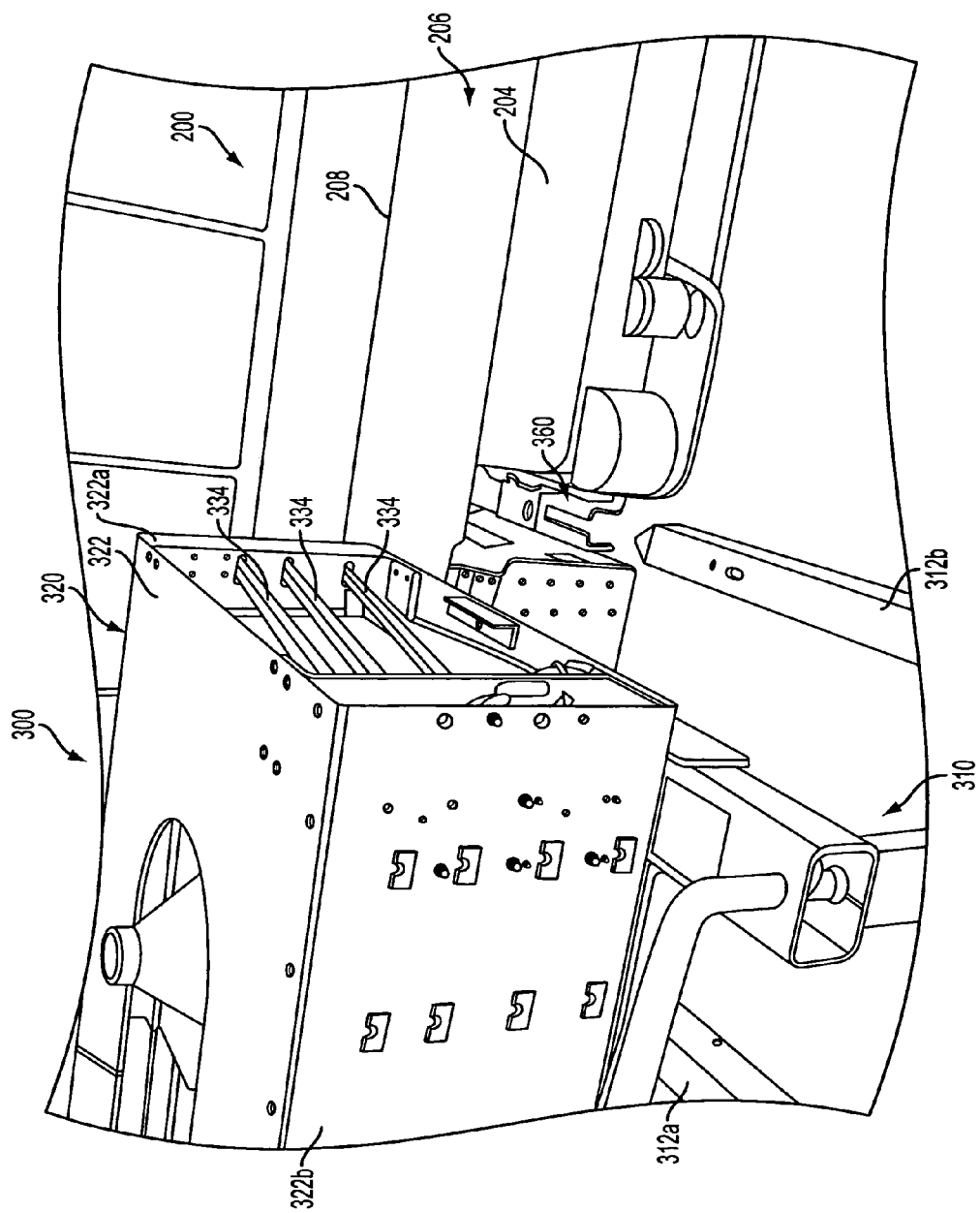
FIG. 14 is a further partial perspective view of the nuclear medicine gantry and patient handling system of FIGS. 1 and 12, illustrating a relative positioning of the collimator change cart of FIGS. 1-3 thereto prior to docking therewith.
Figure 15:
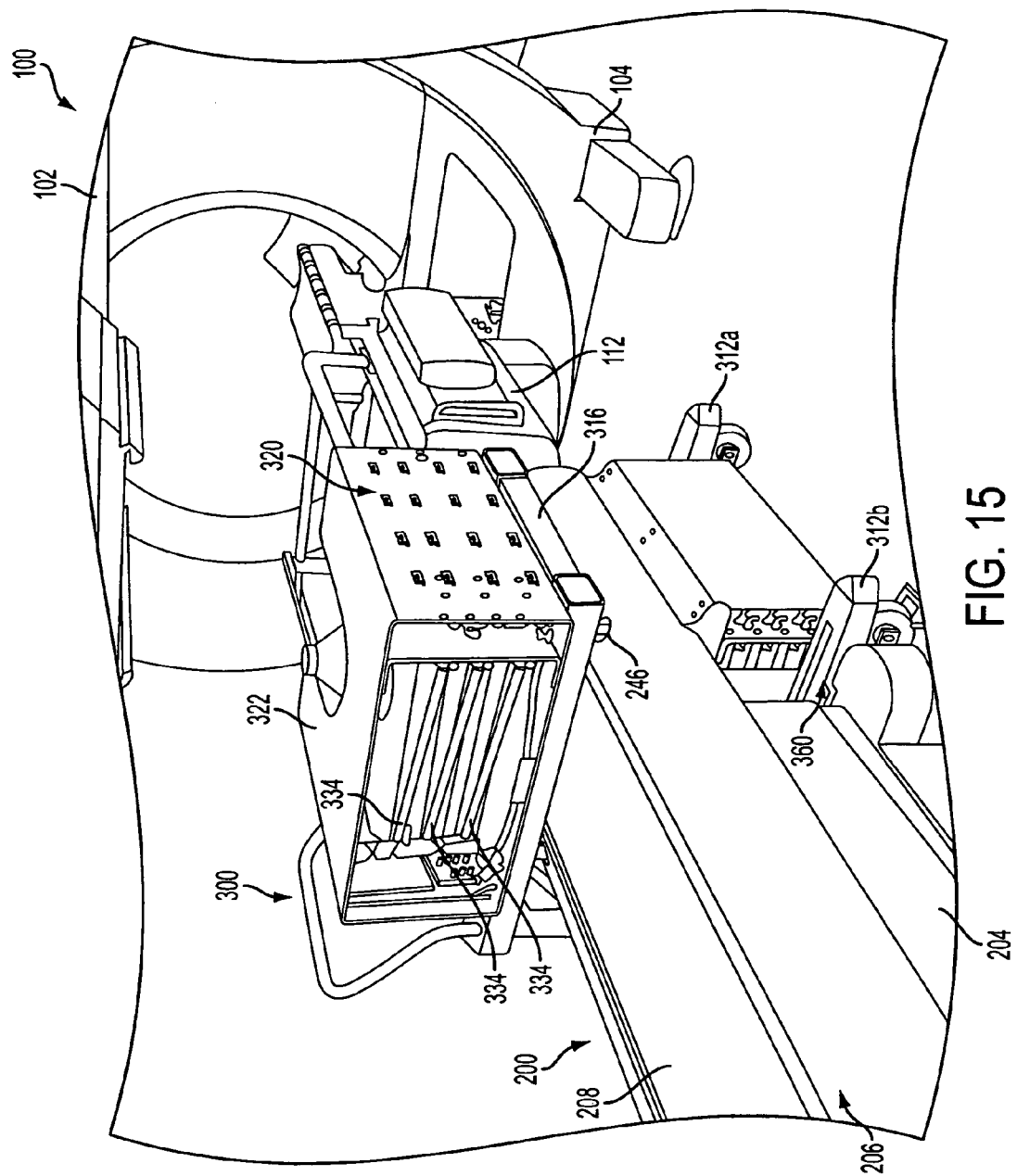
FIG. 15 is a partial perspective view of the nuclear medicine gantry and patient handling system of FIGS. 1 and 12, illustrating a relative positioning of the collimator chance cart of FIGS. 1-3 thereto following docking therewith.

Turning now to FIGS. 12-26, a method of using collimator change cart 300 to change and/or replace a collimator of nuclear camera 112 of nuclear medicine gantry 100 is described. Typically, as seen in FIG. 12, pallet 208 is lowered relative to nuclear medicine gantry 100 to a collimator change position. As seen throughout FIGS. 12-26, with pallet 208 in the collimator change position, collimator change cart 300 is moved into a collimator change or docked position wherein one of lower rails 312a, 312b of cart assembly 310 is aligned with and introduced into channeled rail 362 of anti-tip over element 360. When collimator change cart 300 is in the docked position with respect to patient handling system 200 and nuclear medicine gantry 100, collimator drawer assembly 320 is oriented such that drawers 330 thereof are extendable over nuclear camera 112.

Figure 11:
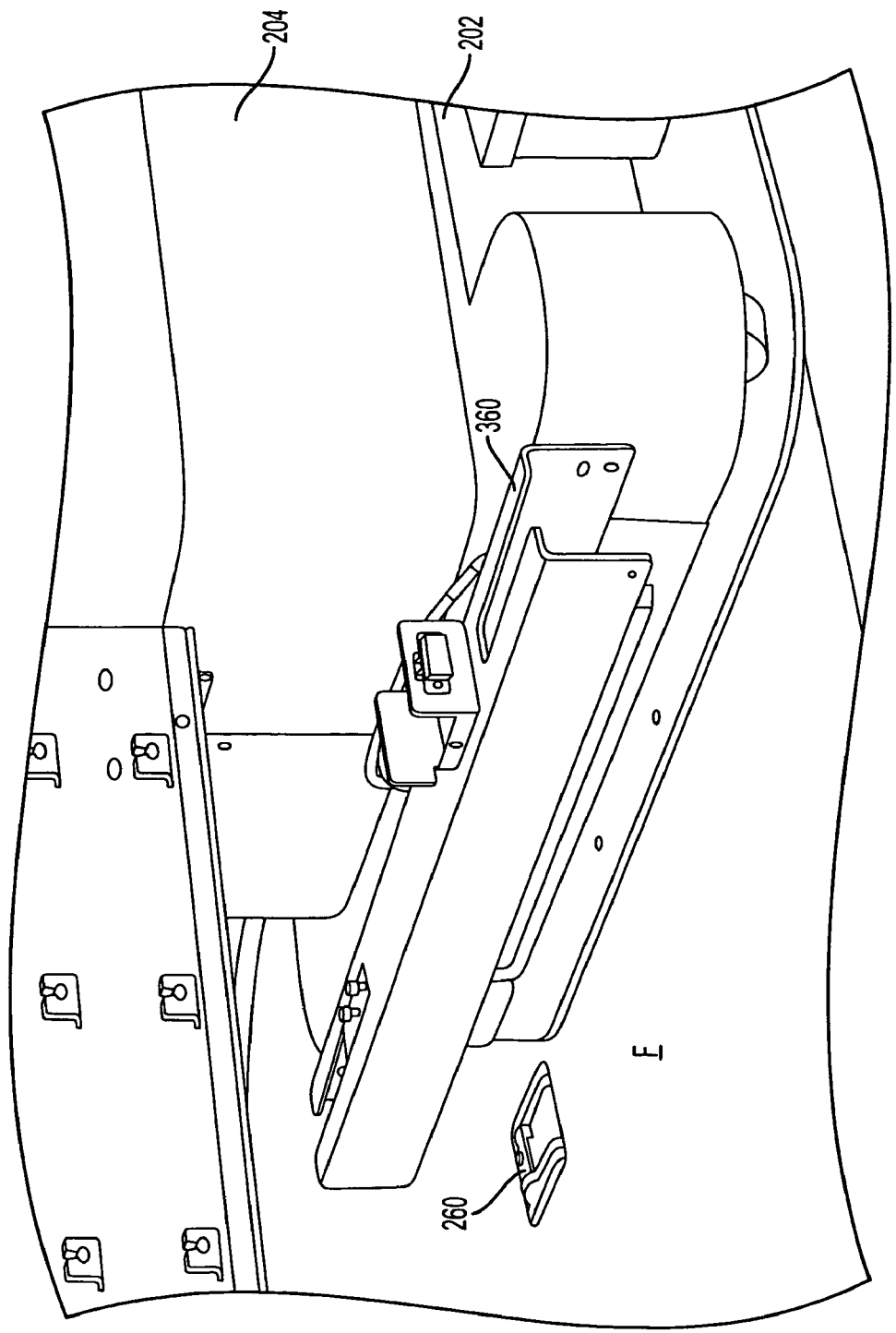
FIG. 11 is an enlarged perspective view of a collimator change cart alignment guide operatively associated with the nuclear medicine gantry and the patient handling system.
Figure 16:
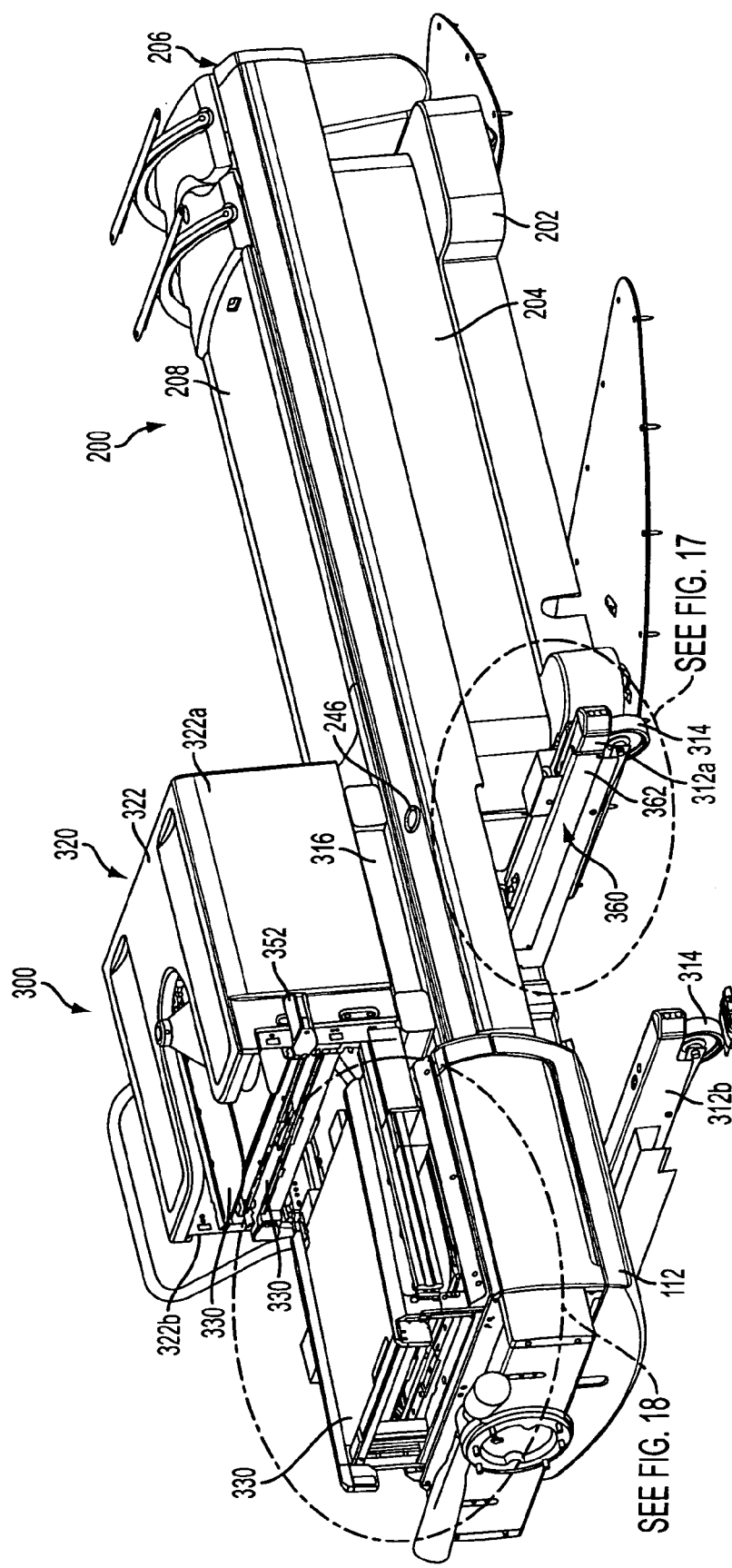
FIG. 16 is a perspective view of the patient handling system of FIGS. 1 and 12, illustrating the collimator change cart of FIGS. 1-3 docket therewith and a collimator change drawer thereof extended over the nuclear camera of the nuclear medicine gantry of FIGS. 1 and 12.
Figure 21:
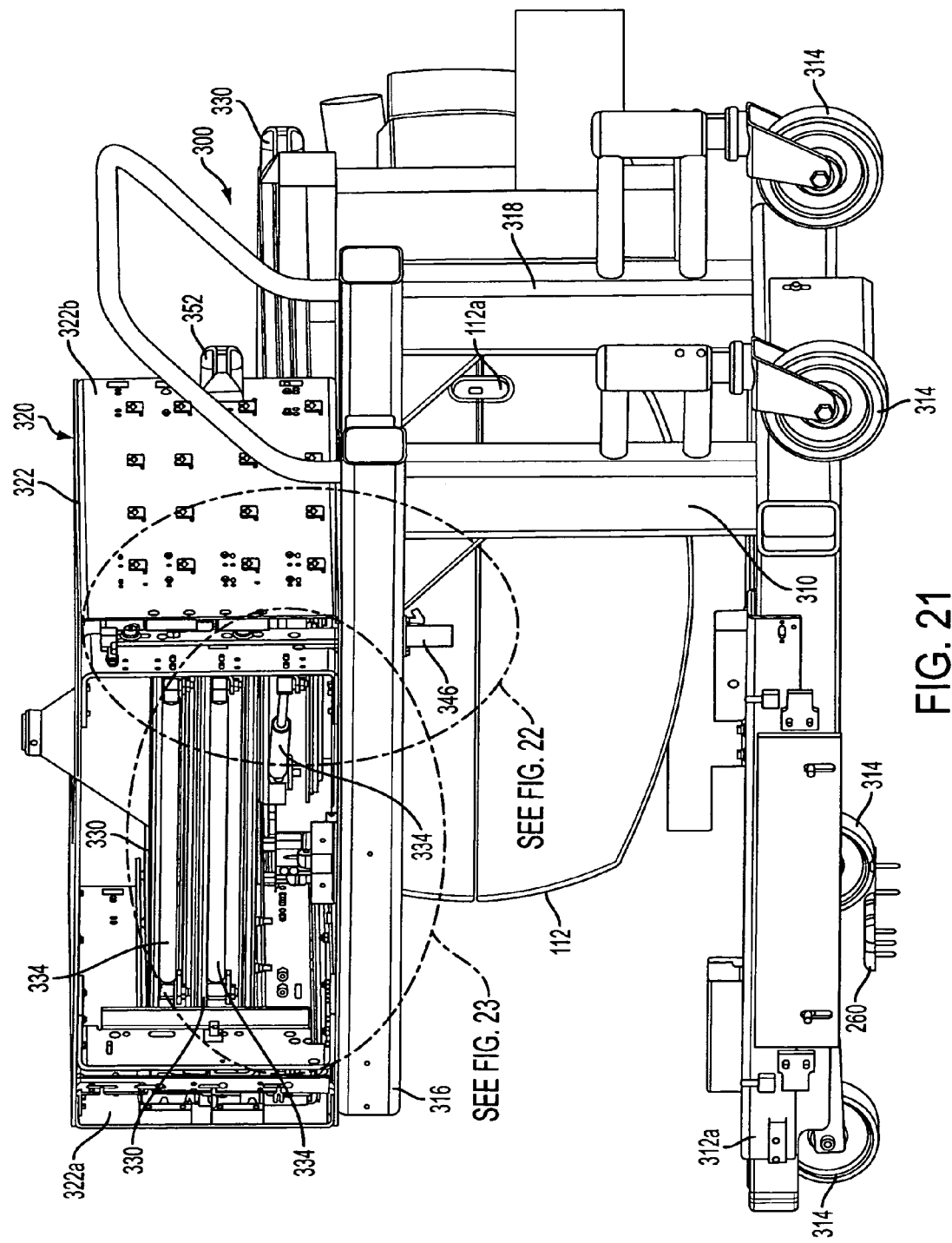
FIG. 21 is a perspective view of the collimator change cart of FIGS. 1-3 docket with the patient handling system.
Figure 22:
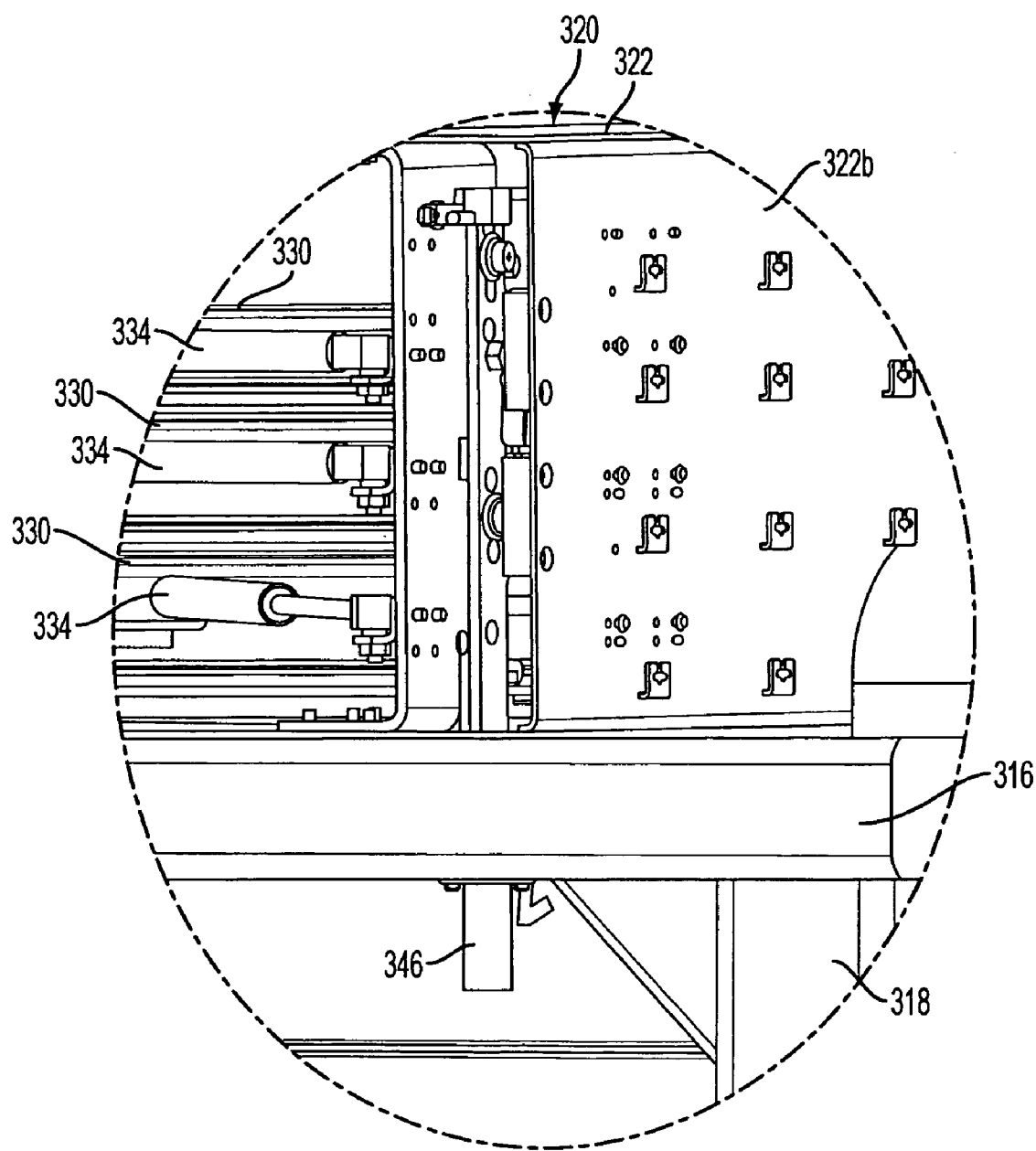
FIG. 22 is an enlarged view of the indicated area of detail of FIG. 21.
Figure 23:
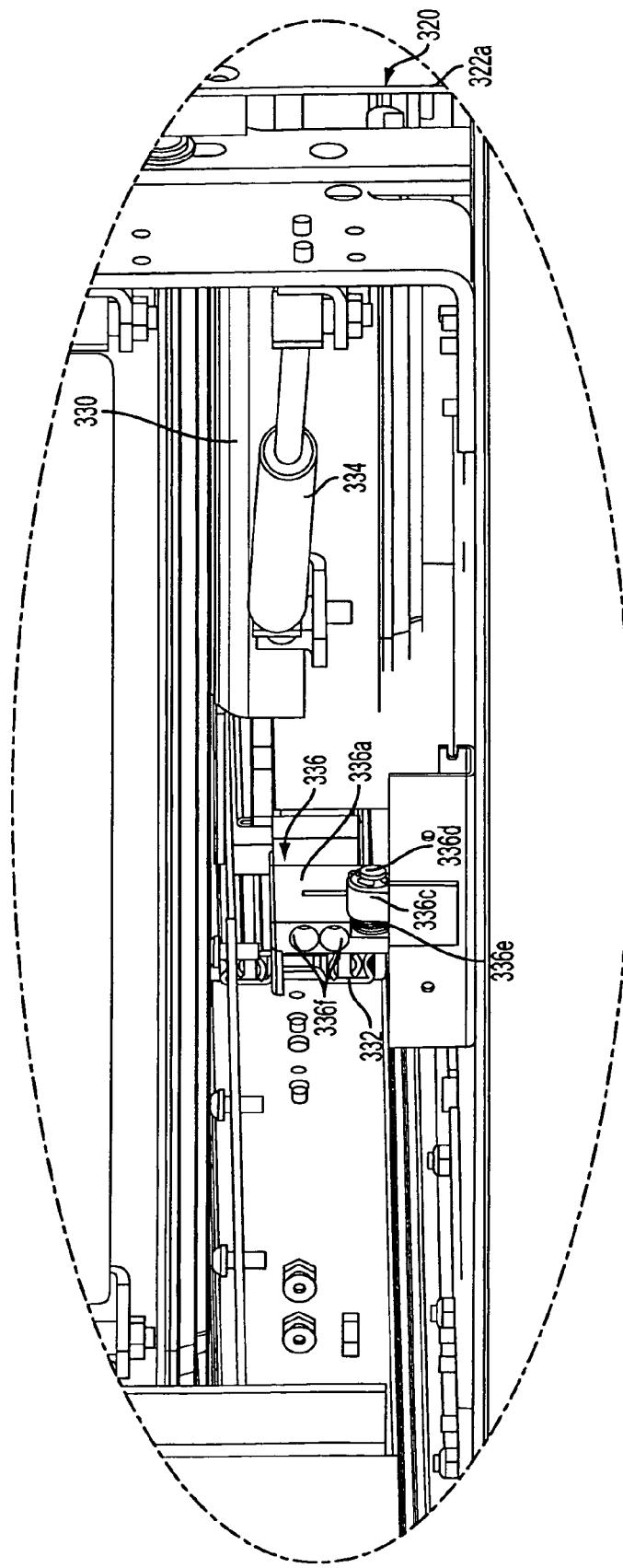
FIG. 23 is an enlarged view of the indicated area of detail of FIG. 21.
Figure 24:
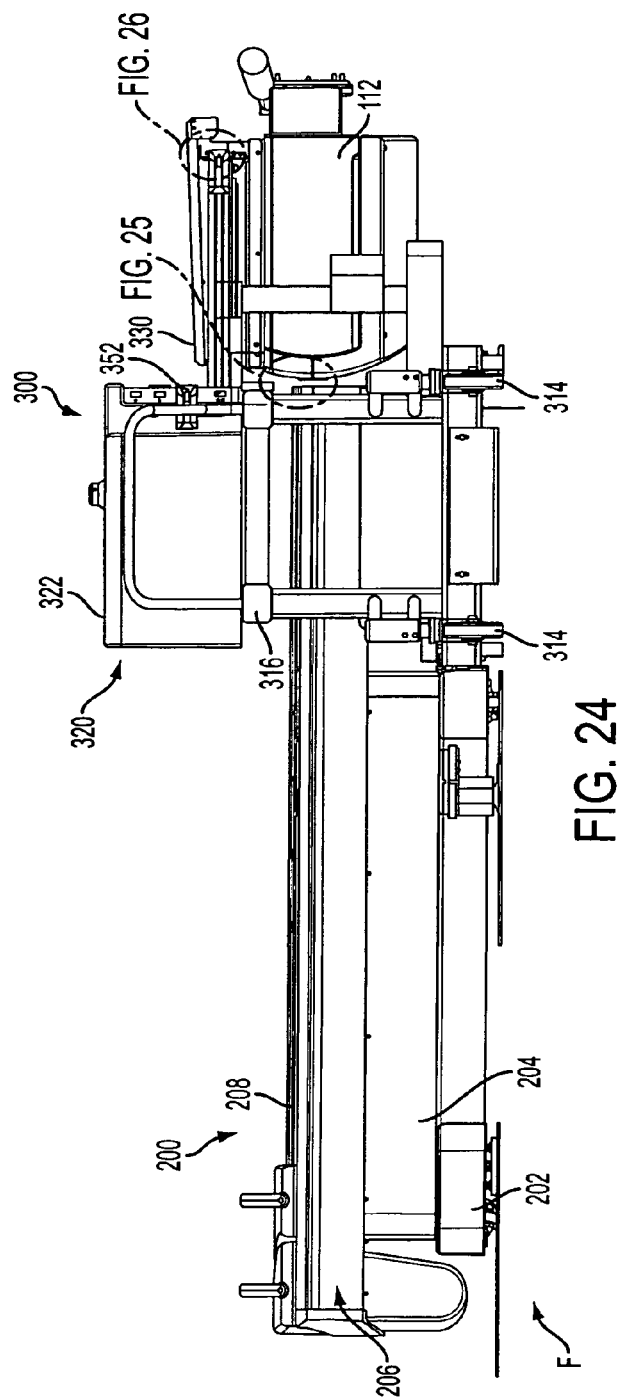
FIG. 24 is a side, elevational view of the collimator change cart of FIGS. 1-3 docket with the patient handling system.

In order to ensure that collimator change cart 300 is in the docked position, as seen in FIG. 11, a sensor pad 260 may be secured to floor "F" at a known location relative to patient handling system 200 and nuclear medicine gantry 100. In this manner, collimator change cart 300 is configured and dimensioned such that when collimator change cart 300 is properly docked, a caster 314 thereof operatively engages sensor pad 260 (i.e., an optical sensor, a pressure sensor, etc.), as shown in FIGS. 16 and 21.

With collimator change cart 300 in the docked position, with respect to patient handling system 200 and nuclear medicine gantry 100, as seen in FIGS. 6 and 7, lock plunger 346 of drawer locking mechanism 340 is aligned with a lock receptacle 246 provided on pallet 208 of patient handling system 200. With collimator change cart 300 in the docked position, pallet 208 of patient handling system 200 is raised until lock receptacle 246 thereof engages lock plunger 346 of drawer locking mechanism 340 and forces lock plunger 346 in an upward direction to the retracted position. In so doing, locking tabs 342a-342c of drawer locking mechanism 340 are moved out of locking engagement with respect to drawers 330, as shown in FIG. 9 and as discussed above. Additionally, lock receptacle 246 captures lock plunger 346 therein and thus further fixes collimator change cart 300 in the docked position.

Figure 26:
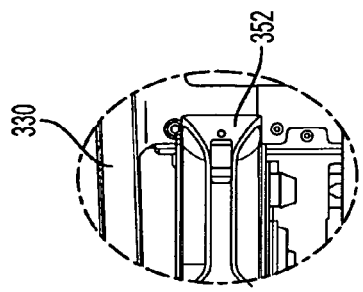
FIG. 26 is an enlarged view of the indicated area of detail of FIG. 24.
Figure 25:
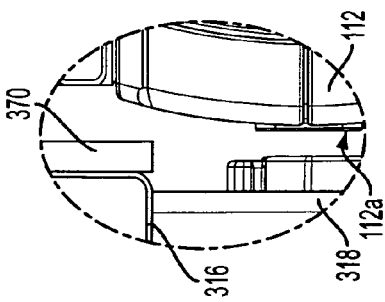
FIG. 25 is an enlarged view of the indicated area of detail of FIG. 24.

With collimator change cart 300 in a fixed docked position, nuclear camera 112 is moved from its "home" position (i.e., a fully lowered position), upwardly until a detector 112a of nuclear camera 112 detects a "home flag" 370 (i.e., a sensor, an optical recognition symbol, etc.) provided on collimator change cart 300, see FIG. 25. In one method, once the "home flag" 370 is located, the desired drawer 330 is opened to a fully extended position and switches (not shown) located on the clamp arms (not shown) are closed, as seen in FIG. 26.

{Please indicate where the clamp arms are located in the drawings}. The closing of the switches located on the clamp arms indicates to a central processor which of drawers 330 has been opened and the additional distance required for nuclear camera 112 to move in order to be in a proper collimator change position/location. As such, nuclear camera 112 is further raised or moved upwardly said known distance until nuclear camera 112 is in the proper collimator change or release position. When nuclear camera 112 is in the proper collimator change or release position, collimator 132 is lifted off of drawer 330 and drawer 330 is free to be retracted into housing 322.

In another method, once the "home flag" 370 is located, the distance to the desired drawer 330 is known and as such, nuclear camera 112 may be further raised or moved to the location of said drawer 330.

Figure 17:
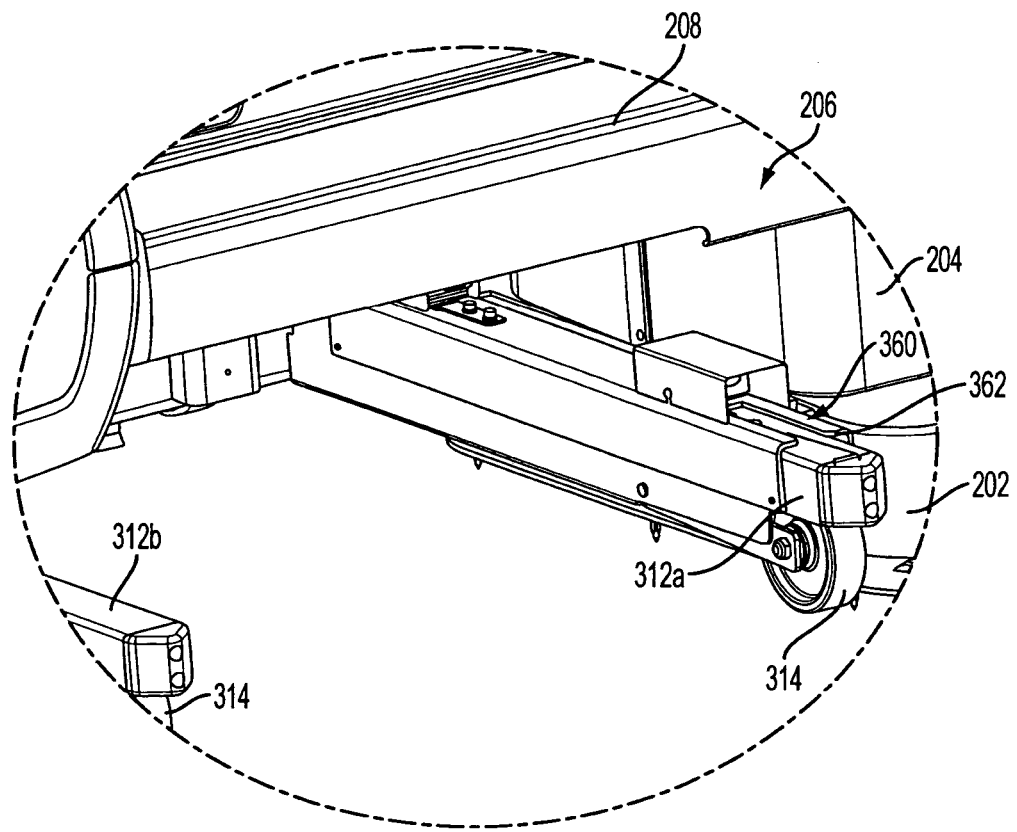
FIG. 17 is an enlarged, perspective view of the indicated area of detail of FIG. 16, illustrating the anti-tip over feature of the present disclosure.
Figure 18:
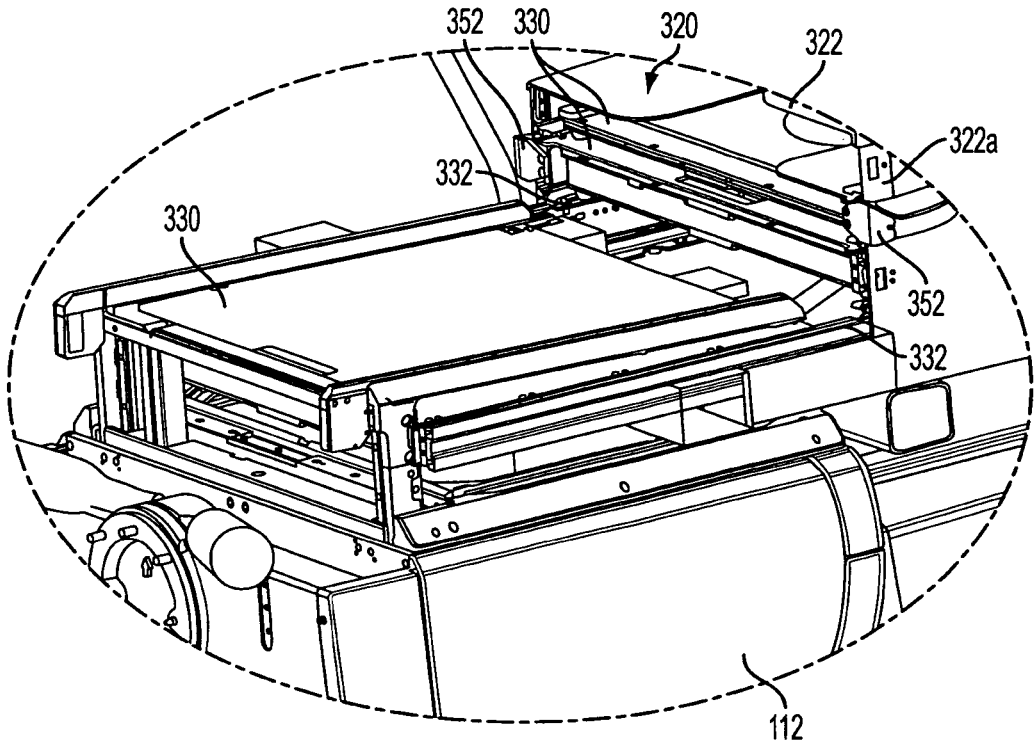
FIG. 18 is an enlarged, perspective view of the indicated area of detail of FIG. 16, illustrating the collimator change drawer of the collimator change cart of FIGS. 1-3 extended over the nuclear camera.
Figure 19:
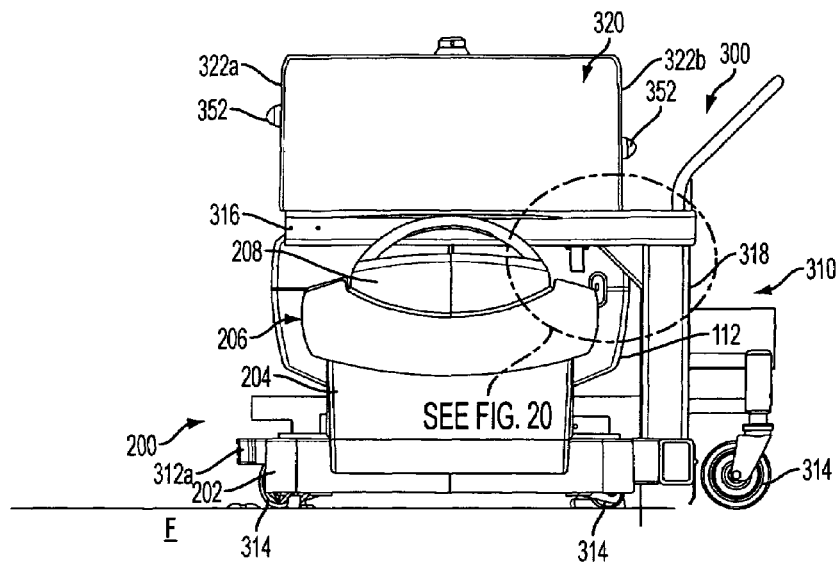
FIG. 19 is an elevational view of the collimator change cart of FIGS. 1-3 docket with the patient handling system.
Figure 20:
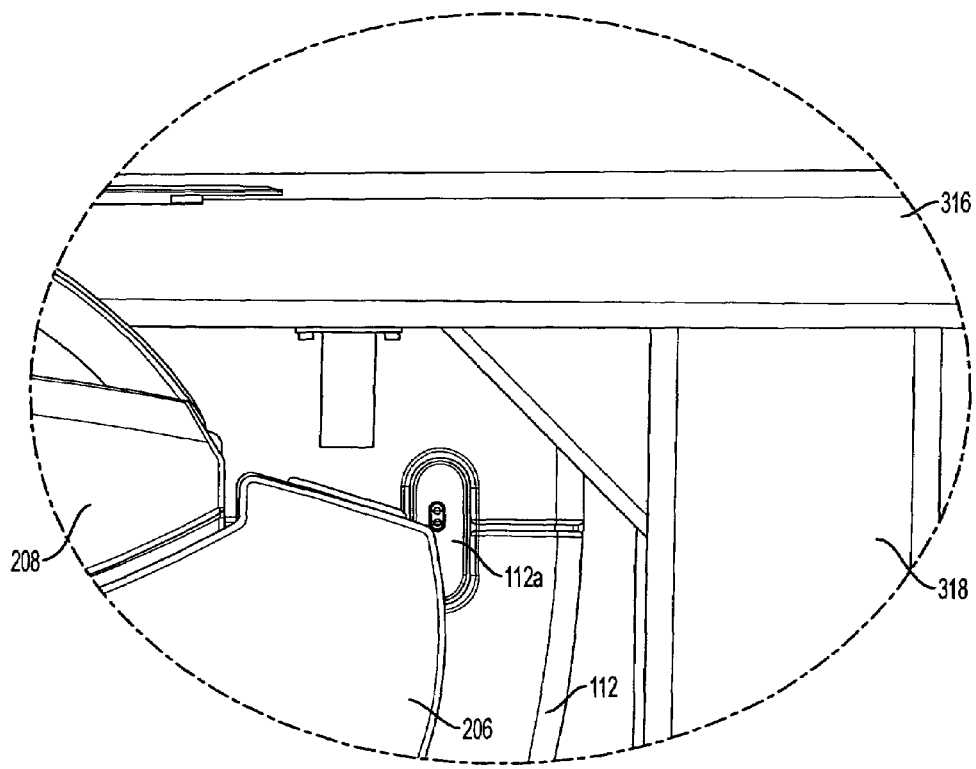
FIG. 20 is an enlarged view of the indicated area of detail of FIG. 19.

In one embodiment, it is envisioned that when nuclear camera 112 is moved to the desired position, as seen in FIG. 19, the drawer lock 350 may be automatically actuated to unlock a respective one of drawers 330a-330d and allow for the respective one of drawers 330a-330d to be opened. As seen in FIGS. 17 and 20, with drawer lock 350 of a respective one of drawers 330a-330d unlocked, the respective one of drawers 330a-330d is withdrawn from housing 322 of collimator drawer assembly 320 to overlie nuclear camera 112.

As discussed above, drawer pusher assembly 336 ensures that the respective one of drawers 330 is withdrawn from housing 322 of collimator drawer assembly 320 in a uniform manner, and damper 334 ensures that the respective one of drawers 330 is not withdrawn from housing 322 of collimator drawer assembly 320 too quickly.

With the respective one of drawers 330 extended over nuclear camera 112, the collimator of nuclear camera 112 may be removed, a collimator may be attached to nuclear camera 112 and/or the collimator of nuclear camera 112 may be replaced as needed and/or desired.

Once the collimator has been removed from nuclear camera 112, attached to nuclear camera 112 and/or replaced, the respective one of the drawers 330 is retracted into housing 322 of collimator drawer assembly 320, nuclear camera 112 is lowered to the "home" position and pallet 208 of patient handling system 200 is also lowered. When pallet 208 is lowered, lock receptacle 246 disengages lock plunger 346 of drawer locking mechanism 340 which returns to an extended condition and which moves locking tabs 342a-342c of drawer locking mechanism 340 into locking engagement with respect to drawers 330. With lock plunger 346 disengaged from lock receptacle 246, collimator change cart 300 is free to be moved out of operative engagement with nuclear medicine gantry 100 and patient handling system 200.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A collimator change cart for operation with a nuclear camera of a nuclear medicine gantry and a patient handling system, the collimator change cart comprising:

a cart assembly; and a collimator drawer assembly supported on the cart assembly, the collimator drawer assembly includes:

a housing;

a plurality of collimator drawers slidably supported in the housing, wherein each drawer is supported on a rail provided on opposed sides of said drawer; and a damper operatively connected to each drawer, wherein the damper slows extension and retraction of drawers into and out of the housing wherein the collimator drawer assembly includes a drawer locking mechanism movable from a first position in which all the drawers are prevented from sliding out of the housing and a second position in which all of the drawers are free to slide out of the housing, wherein the drawer locking mechanism includes a lock plunger extending from a bottom of the housing, wherein the lock plunger is actuatable to move the drawer locking mechanism between the first and second positions.

2. The collimator change cart according to claim 1, wherein the collimator drawer assembly further includes a pusher operatively associated with each drawer, wherein the pusher causes the drawer to extend uniformly from the housing.

3. The collimator change cart according to claim 1, wherein each damper is a hydraulic fluid damper.

4. The collimator change cart according to claim 3, wherein each velocity damper includes a first end connected to a respective drawer and a second end connected to the housing.

5. The collimator change cart according to claim 1, wherein the drawer locking mechanism includes an actuator bar supporting a plurality of tabs thereon, wherein the actuator bar is movable between the drawer locking mechanism first position and second position.

6. The collimator change cart according to claim 5, wherein the tabs are movable between the drawer locking mechanism first position and second position as the actuator bar is moved between the drawer locking mechanism first position and second position.

7. The collimator change cart according to claim 6, wherein each tab engages a respective drawer when the drawer locking mechanism is in the first position.

8. The collimator change cart according to claim 1, wherein the lock plunger engages a lock receptacle on the patient handling system and inhibits tipping of the collimator change cart when the collimator change cart is docked.

9. The collimator change cart according to claim 1, further comprising an anti-tip over feature supported on the patient handling system and configured to engage the cart assembly when the collimator change cart is docked.

10. The collimator change cart according to claim 9, wherein the anti-tip over feature includes a channeled rail supported on the patient handling system and configured and dimensioned to selectively receive at least a portion of the cart assembly therein.

11. The collimator change cart according to claim 10, wherein the anti-tip over feature further includes a plunger extending from a bottom surface of the housing of the collimator change cart, wherein the plunger operatively engages a pallet of the patient handling system when the pallet is in a raised position.

12. The collimator change cart according to claim 11, further comprising a drawer locking mechanism movable from a first position in which all the drawers are prevented from sliding out of the housing and a second position in which all of the drawers are free to slide out of the housing.

13. The collimator change cart according to claim 12, wherein the drawer locking mechanism includes an actuator bar supporting a plurality of tabs thereon, wherein the actuator bar is movable between the drawer locking mechanism first position and second position.

14. The collimator change cart according to claim 13, wherein the plunger is connected to the drawer locking mechanism, wherein the plunger is actuatable to move the drawer locking mechanism between the first and second positions.

15. The collimator change cart according to claim 1, wherein the cart assembly includes a pair of spaced apart lower rails supports on casters.

16. The collimator change cart according to claim 15, wherein the cart assembly includes an upper platform cantilevered with respect to an upright extending from the lower rails.

17. A collimator change cart for operation with a nuclear camera of a nuclear medicine gantry and a patient handling system, the collimator change cart comprising:

a cart assembly; and a collimator drawer assembly supported on the cart assembly, the collimator drawer assembly includes:

a housing;

a plurality of collimator drawers slidably supported in the housing, wherein each drawer is supported on a rail provided on opposed sides of said drawer;

a damper operatively connected to each drawer, wherein the damper slows extension and retraction of drawers into and out of the housing; and a drawer locking mechanism movable from a first position in which all the drawers are prevented from sliding out of the housing and a second position in which all of the drawers are free to slide out of the housing; and an anti-tip over feature supported on the patient handling system and configured to engage the cart assembly when the collimator change cart is in an operative position relative to the nuclear medicine gantry and the patient handling system wherein the drawer locking mechanism includes a lock plunger extending from a bottom of the housing, wherein the lock plunger is actuatable to move the drawer locking mechanism between the first and second positions.

* * * * *